US007592139B2

(12) United States Patent
West et al.

(10) Patent No.: US 7,592,139 B2
(45) Date of Patent: Sep. 22, 2009

(54) HIGH TEMPERATURE FLOW-THROUGH DEVICE FOR RAPID SOLUBILIZATION AND ANALYSIS

(75) Inventors: Jason A. A. West, Castro Valley, CA (US); Kyle W. Hukari, San Ramon, CA (US); Kamlesh D. Patel, Dublin, CA (US); Kenneth A. Peterson, Albuquerque, NM (US); Ronald F. Renzi, Tracy, CA (US)

(73) Assignee: Sandia National Laboratories, Liverpool, CA (US)

( * ) Notice: Subject to any disclaimer, the term of this patent is extended or adjusted under 35 U.S.C. 154(b) by 55 days.

(21) Appl. No.: 11/059,079

(22) Filed: Feb. 16, 2005

(65) Prior Publication Data

US 2009/0215023 A1 Aug. 27, 2009

Related U.S. Application Data

(60) Provisional application No. 60/612,969, filed on Sep. 24, 2004.

(51) Int. Cl.
*C12Q 1/68* (2006.01)
*C12M 1/34* (2006.01)

(52) U.S. Cl. .......................................... 435/6; 435/287.1

(58) Field of Classification Search .............. 435/287.2, 435/6, 287.1; 536/23.1, 22.1
See application file for complete search history.

(56) References Cited

U.S. PATENT DOCUMENTS 4,591,463 A * 5/1986 Nahra et al. ................ 261/116
4,908,112 A 3/1990 Pace ........................... 204/299
5,061,336 A 10/1991 Soane ........................ 156/245
5,071,531 A 12/1991 Soane ........................ 204/616
5,132,012 A 7/1992 Miura et al. ............. 210/198.2
5,135,627 A 8/1992 Soane ........................ 204/455
5,194,133 A 3/1993 Clark et al. ................ 208/299
5,458,761 A 10/1995 Kamahori et al. ....... 204/299 R
5,532,139 A 7/1996 Miller ......................... 435/29
5,569,364 A 10/1996 Hooper et al. .............. 204/455
5,571,410 A 11/1996 Swedberg et al. ........ 210/198.2
5,580,990 A 12/1996 Van den Berg et al. ...... 549/212
5,605,662 A 2/1997 Heller et al. ............... 422/68.1
5,631,337 A 5/1997 Sassi et al. ............... 526/307.2
5,632,957 A 5/1997 Heller et al. ............... 422/68.1
5,770,365 A 6/1998 Lane et al. ..................... 435/6
5,800,690 A 9/1998 Chow et al. ................. 204/451
5,824,204 A 10/1998 Jerman ....................... 204/601
5,824,224 A 10/1998 Fujishiro et al. ............ 210/651
5,914,255 A * 6/1999 Grae ....................... 435/173.1
5,929,208 A 7/1999 Heller et al. ................ 530/333
5,955,295 A 9/1999 Miller ......................... 435/29
6,001,229 A 12/1999 Ramsey ...................... 204/451
6,017,696 A 1/2000 Heller ........................... 435/6
6,051,380 A 4/2000 Sosnowski et al. ............. 435/6
6,133,038 A 10/2000 Houthoff et al. .............. 436/84
6,156,576 A * 12/2000 Allbritton et al. ............. 436/63
6,210,896 B1 4/2001 Chan ............................ 435/6
6,231,812 B1 5/2001 Rothberg et al. ........... 422/68.1
6,238,624 B1 5/2001 Heller et al. ............... 422/68.1
6,245,508 B1 6/2001 Heller et al. ................... 435/6
6,258,606 B1 7/2001 Kovacs ....................... 436/149
6,270,641 B1 8/2001 Griffiths et al. ............. 204/451
6,274,726 B1 8/2001 Laugharn, Jr. et al. ..... 536/25.4
6,284,117 B1 9/2001 Smolko et al. .............. 204/543
6,290,909 B1 9/2001 Paul et al. ..................... 422/70
6,309,601 B1 10/2001 Juncosa et al. ............. 422/68.1
6,315,953 B1 11/2001 Ackley et al. .............. 422/68.1
6,316,608 B1 11/2001 Reynolds et al. ........... 536/22.1
6,329,209 B1 12/2001 Wagner et al. .............. 436/518
6,335,201 B1 1/2002 Allbritton et al. ............. 436/63
6,355,420 B1 3/2002 Chan ............................ 435/6
6,365,418 B1 4/2002 Wagner et al. .............. 436/518
6,379,970 B1 4/2002 Liebler et al. ................. 436/86
6,403,311 B1 6/2002 Chan ............................ 435/6
6,403,367 B1 6/2002 Cheng et al. ............. 435/287.1
6,406,921 B1 6/2002 Wagner et al. .............. 436/518
6,432,361 B1 8/2002 Rothberg et al. ........... 422/68.1
6,472,443 B1 10/2002 Shepodd ...................... 521/63
6,475,364 B1 11/2002 Dubrow et al. .............. 204/455
6,475,809 B1 11/2002 Wagner et al. .............. 436/518
6,499,499 B2 12/2002 Dantsker et al. ............... 137/1

(Continued)

FOREIGN PATENT DOCUMENTS

EP 1 385 006 A2 1/2004

(Continued)

OTHER PUBLICATIONS

"Gene Logic Chip Patents" Micropatent Search Report created on May 7, 2004.
"MetriGenix" Micropatent Search Report created on May 7, 2004.
"Nanogen (Chips and Devices)" Micropatent Search Report created on May 7, 2004.
"Combimatrix" Micropatent Search Report created on May 7, 2004.
"Zyomyx" Micropatent Search Report created on May 7, 2004.
Ramachandran, N. et al., "Self-Assembling Protein Microarrays," *Science*, Jul. 2, 2004, 305(5680): 86-90 [abstract only].
Alarie, J.P. et al., "Electroosmotically Induced Hydraulic Pumping on Microchips", *Micro Total Analysis Systems*, 2001, 131-132.

(Continued)

*Primary Examiner*—Suryaprabha Chunduru
(74) *Attorney, Agent, or Firm*—Woodcock Washburn, LLP

(57) ABSTRACT

Devices and methods for thermally lysing of biological material, for example vegetative bacterial cells and bacterial spores, are provided. Hot solution methods for solubilizing bacterial spores are described. Systems for direct analysis are disclosed including thermal lysers coupled to sample preparation stations. Integrated systems capable of performing sample lysis, labeling and protein fingerprint analysis of biological material, for example, vegetative bacterial cells, bacterial spores and viruses are provided.

20 Claims, 20 Drawing Sheets

U.S. PATENT DOCUMENTS

| | | | |
|---|---|---|---|
| 6,518,022 B1 | 2/2003 | Sosnowski et al. | 435/6 |
| 6,544,734 B1 | 4/2003 | Briscoe et al. | 435/6 |
| 6,551,784 B2 | 4/2003 | Fodor et al. | 435/6 |
| 6,567,163 B1 | 5/2003 | Sandstrom | 356/317 |
| 6,569,685 B1 | 5/2003 | Carlson et al. | 436/86 |
| 6,572,830 B1 * | 6/2003 | Burdon et al. | 422/186.29 |
| 6,582,660 B1 | 6/2003 | Heller et al. | 422/68.1 |
| 6,613,525 B2 | 9/2003 | Nelson et al. | 435/6 |
| 6,664,104 B2 | 12/2003 | Pourahmadi et al. | 435/288.6 |
| 6,670,194 B1 | 12/2003 | Aebersold et al. | 436/173 |
| 6,726,880 B1 | 4/2004 | Ackley et al. | 422/68.1 |
| 6,743,630 B2 | 6/2004 | Sato | 435/402 |
| 6,773,909 B2 | 8/2004 | Monica et al. | 435/235.1 |
| 6,780,582 B1 | 8/2004 | Wagner et al. | 435/6 |
| 6,818,112 B2 | 11/2004 | Schneider et al. | 204/450 |
| 6,846,638 B2 | 1/2005 | Shipwash | 435/7.1 |
| 6,852,544 B2 | 2/2005 | Aebersold et al. | 436/173 |
| 6,927,025 B1 | 8/2005 | Carr et al. | 435/6 |
| 6,939,696 B1 | 9/2005 | Llorin et al. | 435/173.1 |
| 6,969,614 B1 | 11/2005 | Liotta et al. | 436/177 |
| 6,969,757 B2 | 11/2005 | Haynes et al. | 530/327 |
| 6,974,526 B2 | 12/2005 | Lee et al. | 204/451 |
| 7,045,296 B2 | 5/2006 | Parker et al. | 435/7.1 |
| 2001/0008212 A1 | 7/2001 | Shepodd et al. | 204/451 |
| 2001/0052976 A1 | 12/2001 | Juncosa et al. | 356/307 |
| 2002/0004204 A1 | 1/2002 | O'Keefe | 435/6 |
| 2002/0028471 A1 | 3/2002 | Oberhardt | 435/7.21 |
| 2002/0028503 A1 | 3/2002 | Ackley et al. | 435/287.2 |
| 2002/0036142 A1 | 3/2002 | Gascoyne et al. | 204/547 |
| 2002/0037542 A1 | 3/2002 | Allbritton et al. | 435/7.23 |
| 2002/0064794 A1 | 5/2002 | Leung et al. | 435/6 |
| 2002/0095073 A1 | 7/2002 | Jacobs et al. | 600/300 |
| 2002/0106686 A1 | 8/2002 | McKernan | 435/6 |
| 2002/0127565 A1 | 9/2002 | Cunningham et al. | 435/6 |
| 2002/0131899 A1 | 9/2002 | Kovacs | 422/820.1 |
| 2002/0141903 A1 | 10/2002 | Parunak et al. | 422/101 |
| 2002/0155586 A1 | 10/2002 | Cheng et al. | 435/287.1 |
| 2002/0164628 A1 | 11/2002 | Kurn | 435/6 |
| 2002/0194909 A1 | 12/2002 | Hasselbrink, Jr. et al. | 73/253 |
| 2002/0197631 A1 | 12/2002 | Lawrence et al. | 435/6 |
| 2003/0027354 A1 | 2/2003 | Geli | 436/178 |
| 2003/0048933 A1 | 3/2003 | Brown et al. | 382/128 |
| 2003/0075446 A1 | 4/2003 | Culbertson et al. | 204/451 |
| 2003/0075491 A1 | 4/2003 | Griffiths | 210/198.2 |
| 2003/0082604 A1 | 5/2003 | Swanson et al. | 435/6 |
| 2003/0116552 A1 | 6/2003 | Santorovo et al. | 219/209 |
| 2003/0146100 A1 | 8/2003 | Huang et al. | 204/547 |
| 2003/0151735 A1 | 8/2003 | Blumenfeld et al. | 356/73 |
| 2003/0170810 A1 | 9/2003 | Vedadi et al. | 435/69.1 |
| 2003/0175947 A1 | 9/2003 | Liu et al. | 435/288.5 |
| 2004/0011650 A1 | 1/2004 | Zenhausern et al. | 204/547 |
| 2004/0033530 A1 | 2/2004 | Awrey et al. | 435/6 |
| 2004/0052929 A1 | 3/2004 | Kirby et al. | 427/58 |
| 2004/0058423 A1 | 3/2004 | Albritton et al. | 435/173.7 |
| 2004/0072151 A1 | 4/2004 | Arisawa et al. | 435/5 |
| 2004/0101895 A1 | 5/2004 | Fomovskaia et al. | 435/6 |
| 2004/0106189 A1 | 6/2004 | Dodgson et al. | 435/285.2 |
| 2004/0126279 A1 | 7/2004 | Renzi et al. | 422/100 |
| 2004/0265889 A1 | 12/2004 | Durham et al. | 435/6 |
| 2005/0014134 A1 | 1/2005 | West et al. | 435/5 |
| 2005/0095602 A1 | 5/2005 | West et al. | 435/6 |

FOREIGN PATENT DOCUMENTS

| | | |
|---|---|---|
| EP | 1 385 006 A3 | 1/2004 |
| JP | 11 271 193 A2 | 10/1999 |
| JP | 2002-286643 | 10/2002 |
| WO | WO 97/12030 A1 | 4/1997 |
| WO | WO 98/44351 A | 10/1998 |
| WO | WO 98/49543 A1 | 11/1998 |
| WO | WO 99/15621 A1 | 4/1999 |
| WO | WO 99/18433 A1 | 4/1999 |
| WO | WO 00/09722 A2 | 2/2000 |
| WO | WO 00/09722 A3 | 2/2000 |
| WO | WO 00/30422 A2 | 6/2000 |
| WO | WO 00/62931 A1 | 10/2000 |
| WO | WO 00/79326 A1 | 12/2000 |
| WO | WO 01/07910 A1 | 2/2001 |
| WO | WO 01/44875 A2 | 6/2001 |
| WO | WO 01/44875 A3 | 6/2001 |
| WO | WO 01/45843 A3 | 6/2001 |
| WO | WO 01/53799 A1 | 7/2001 |
| WO | WO 01/69302 A2 | 9/2001 |
| WO | WO 02/40630 | 5/2002 |
| WO | WO 02/065125 A1 | 8/2002 |
| WO | WO 03/004162 A1 | 1/2003 |
| WO | WO 03/036298 A2 | 5/2003 |
| WO | WO 03/036298 A3 | 5/2003 |
| WO | WO 03/093791 | 11/2003 |
| WO | WO2005/011867 A2 | 2/2005 |

OTHER PUBLICATIONS

Cheek, B.J. et al., "Chemiluminescence Detection for Hybridization Assays on the Flow-Thru Chip, a Three-Dimensional Microchannel Biochip", *Anal Chem*, 2001, 73, 5777-5783.

Doermann, A.H., "Genetic Control of Capsid Length in Bacteriophage T4. Isolation and Preliminary Description of Four New Mutants", *J. Virol*, 1973, 12(2), 374-385.

Gerritsen, V.B. "Baneful Beans", *Protein Spotlight*, 2003, 31, 2 pages.

Kustos, I. et al., "Capillary Electrophoretic Analysis of Wild Type and Mutant *Proteus penneri* Outer Membrane Proteins", *Electrophoresis*, 2000, 21, 3020-3027.

Kustos, I. et al., "Protein Profile Characterization of Bacterial Lysates by Capillary Electrophoresis", *Electrophoresis*, 1998, 19(13), 2317-2323.

Panaro, N.J. et al., "Evaluation of DNA Fragment Sizing and Quantification by the Agilent 2100 Bioanalyzer", *Clinical Chemistry*, 2000, 46(11), 1851-1853.

Schena, M. et al., "Quantitative Monitoring of Gene Expression Patterns with a Complementary DNA Microarray", *Science*, 1995, 270, 467-470.

Svec, F., "Porous Monoliths: The Newest Generation of Stationary Phases for HPLC and Related Methods", *Recent Developments in LC Coulmn Technology*, Jun. 2003, 2-6.

Yu, C. et al., "Monolithic Porous Polymer for On-Chip Solid-Phase Extraction and Preconcentration Prepared by Photoinitiated in Situ Polymerization within a Microfluidic Device", *Anal. Chem.* 2001, 73, 5088-5096.

Yu, C. et al., "Towards Stationary Phases for Chromatography on a Microchip: Molded Porous Polymer Monoliths Prepared in Capillaries by Photoinitiated in situ Polymerization as Separation Media for Electrochromatography", *Electrophoresis*, 2000, 21, 120-127.

"Agilent Technologies Launches AgBio Program with Introduction of Industry's First Microarray to Include Genetic Probes from Two Species", May 15, 2003, 2 pages.

Welcome to MetriGenex. Escape from the Flatland of Microarrays, http://www.metrigenix.com, 30 pages.

"The Scientist, HANAA to Aid Weapons Inspectors", Nov. 28, 2002, http://www.biomedcentral.com/news/20021128/06, 3 pages.

Kreatech-Legal Information, http://www.kreatech.com/legal.html, May 14, 2003, 7 pages.

Kreatech-Science News 2, http://www.kreatech.com/news/news-ssc2.html, May 14, 2003, 10 pages.

Microfluidics-Reversed Chromatography ON for Chem/Bio Warfare Agent Detection, http://www.ca.sandia.gov/microchem/microfluidics/chembiowar.html, 2 pages.

Available Techs: Monolithic Polymers Revolutionize Microfluidic Devices, http://www.lbl.gov/Tech-Transfer/collaboration/techs/lbn11739.html, May 19, 2003, 2 pages.

"Microarrays: Chipping Away at the Mysteries of Science and Medicine", http://www.ncbi.nlm.nih.gov/About/primer/microarrays.html, May 9, 2003, 11 pages.

Garland, B., M.S., J.D., "Bioethics and Bioterrosism", *The Journal of Philospohy, Science and Law*, Mar. 2002, 2, http//www.psljournal.com/archive/newsedit/bioethics_bioterrorism.cfm, 14 pages.
Sandia seeks Commercialization Partners for Hand-Held Chemical Analysis and Detection System, http://www.sandia.gov/news-center/news-release/2003/mat-chem/chempartners.html, Oct. 7, 2003, 3 pages.
Becker, H. et al., "Polymer Hot Embossing with Silicon Master Structures", *Sensors and Materials*, 1999, 11(5),297-304.
Duffy, D.C. et al., Rapid Prototyping of Microfluidic Systems in Poly(dimethylsiloxane), *Anal Chem.*, 1998, 70, 4974-4984.
Thomas, G.A. et al., "μChemLab™-An Integrated Microanalytical System for Chemical Analysis Using Parallel Gas and Liquid Phase Microseparations", *Proc. SPIE*, 1999, 3713, 66-76.
Chip-Camera Combo Tracks Viruses, *Technology Research News*, Apr. 7, 2004, http://www.technologyreview.com/articles/mb, 2 pages.
Vandernoot, V. et al., "Incorporation of Sample Preconcentration into the μChemLab™/CB Platform for Enhanced Sensitivity", Oral Disclosure, HPCE 2003, 1 page.
MicroPatent Search Report created Sep. 14, 2004. Search Criteria: Text: capillary OR tube 44 pages.
MicroPatent Search Report created Sep. 14, 2004. Search Criteria: "lyser and non-queous and thermal," 156 pages.
MicroPatent Search Report created Sep. 15, 2004. Search Criteria: (lys OR disrupt). 240 pages.
Farchaus, J.W. et al., "Fermentation, Purification, and Characterization of Protective Antigen from a Recombinant, Avirulent Strain of *Bacillus anthracis", Applied and Environmental Microbiology*, 1998, 64(3), 982-991.
Yates, S. et al., "Quantitative Detection of Hepatitis B Virus DNA by Real-Time Nucleic Acid Sequence-Based Amplification with Molecular Beacon Detection", *Journal of Clinical Microbiology*, 2001, 39(10), 3656-3665.
Khan, I.U. et al., "Development of a Single-Tube, Cell Lysis-Based, genus-Specific PCR Method for Rapid Identification of Mycobacteria: Optimization of Cell Lysis: PCR Primers and Conditions, and Restriction Pattern Analysis", *Journal of Clinical Microbiology*, 2004, 42(1), 453-457.
Patel, K. et al., "Low-temperature Cofired Ceramic Substrate Technology for Microfluidic Systems," Sandia National Laboratories, Feb. 16, 2005.
Renzi, R. F. et al., "Hand-Held Microanalytical Instrument for Chip-Based Electrophoretic Separations of Proteins," *Anal Chem*, Dec. 13, 2004, 77(2), 435-441 (abstract only).
CAPLUS search report dated Sep. 15, 2004. © 2004 ACS on STN.
Anderson, A.B. et al., "Subcellular Metabolite Profiles of the Parent CCRF-CEM and the Derived CEM/C2 Cell Lines after Treatment with Doxorubicin", *Journal of Chromatography, B: Analytical technologies in the Biomedical and Life Sciences*, 2004, 808(2), 295-302 [Abstract only—see p. 1 of CAPLUS search report].
Sun, X. et al., "Measurement of Alkaline Phosphatase Isoenzymes in Individual Mosue Marrow Fibroblast Cells based on Capillary Electrophoresis with on-Capillary Enzyme-Catalyzed Reaction and Electrochemical Detection", *Electrophoresis*, 2004, 25(12), 1860-1866 [Abstract only—see p. 2 of CAPLUS search report].
LeFloch, F. et al., "HPCE Monitoring of the N-Glycosylation Pattern and Sialylation of Murine Erythropoietin Produced by CHO Cells in Batch Processes", *Bitotechnology Progress*, 2004, 20(3), 864-871 [Abstract only—see p. 3 of CAPLUS search report].
Lanigan M.D. et al., "Mycobacterial Proteome Extraction: Comparasion of Disruption Methods", *Proteomics*, 2004, 4(4), 1094-1100 [Abstract only—see p. 4 of CAPLUS search report].
Khan, I.U. et al., "Development of a Single-Tube, Cell Lysis-Based, genus-Specific PCR Method for Rapid Identification of Mycobacteria: Optimization of Cell Lysis: PCR Primers and Conditions, and Restriction Pattern Analysis", *Journal of Clinical Microbiology*, 2004, 42(1), 453-457 [Abstract only—see p. 5 of CAPLUS search report].
Gao, Jian, et al., "Integration of Single Cell Injection, Cell Lysis, Separation and Detection of Intracellular Constituents on a Microfluidic Chip", Lab on a Chip, *Royal Society of Chemistry*, 2004, 4(1), 47-52 [Abstract only—see p. 6 of CAPLUS search report].
Malorny, B. et al., "Interlaboratory Diagnostic Accuracy of a Salmonella Specific PCR-Based Method", *International Journal of Food Microbiology*, 2003, 89(2-3), 241-249 [Abstract only—see p. 7 of CAPLUS search report].
Gao, J. et al., "Single Cell Injection and Lysis on a Microfluidic Chip", *Gaodeng Xuexiao Huaxue Xuebao*, 2003, 24(9), 1582-1584 [Abstract only—see p. 9 of CAPLUS search report].
McClain, M.A. et al., "Microfluidic Devices for the High-Throughput Chemical Analysis of Cells", *Analytical Chemistry*, 2003, 75(21), 5646-5655 [Abstract only—see p. 10 of CAPLUS search report].
Han, F. et al., "Fast Electrical Lysis of Cells for Capillary Electrophoresis", *Analytical Chemistry*, 2003, 75(15), 3688-3696 [Abstract only—see p. 11 of CAPLUS search report].
Angelini, A. et al., "New Method for the Extraction of DNA from White Blood Cells for the Detection of Common genetic Variants Associated with Thrombophilia", *Pathophysiology of Haemostasis and Thrombosis*, 2003, 32(4), 180-183 [Abstract only—see p. 12 of CAPLUS search report].
Starkey, D.E. et al., "Determination of Endogenous Extracellular Signal-Regulated Protein Kinase by Microchip Capillary Electrophoresis", *Analytical Biochemistry*, 2003, 316(2), 181-191 [Abstract only—see p. 13 of CAPLUS search report].
Moon, B.G. et al., "Capillary Electrophoresis of Microbes", *Bulletin of the Korean Chemical Society*, 2003, 24(1), 81-85 [Abstract only—see p. 16 of CAPLUS search report].
Shih, Y-P. et al., "High-Throughput Screening of Soluble Recombinant Proteins", *Protein Science*, 2002, 11(7), 1714-1719 [Abstract only—see p. 19 of CAPLUS search report].
Chaiyasut, C. et al., "Red Blood Cell Lysis at the Single Cell Level by Using a Mini Electrophoresis Apparatus", *Chromatography*, 2002, 23(1), 33-38 [Abstract only—see p. 21 of CAPLUS search report].
Ciriacks, C. et al., "Separation and Detection of Doxorubicin Metabolites in Sub-Cellular Fractions using Capillary Electrophoresis with Laser Induced Fluorescence", *Abstracts of Papers, 223rd ACS National Meeting*, Apr. 7-11, 2002, American Chemical Society: Washington, DC [Abstract only—see p. 23 of CAPLUS search report].
Anderson, A.B. et al., "Detection of Doxorubicin and Metabolites in Cell Extracts and in Single Cells by Capillary Electrophoresis with Laser-Induced Fluorescence Detection", *Journal of Chromatography, B: Analytical technologies in the Bimedical and Life Sciences*, 2002, 769(1), 97-106 [Abstract only—see p. 24 of CAPLUS search report].
Nojiri, H. et al., "Rapid, Sensitive, and Accurate Monitoring Method for Auguments Dioxin-Degrading Bacteria", *International in Situ and On-Site Bioremediation Symposium*, Jun. 4-7, 2001, 4, 51-58 [Abstract only—see p. 25 of CAPLUS search report].
Zabzdyr, J.L. et al., "Measurement of Single-Cell Gene Expression Using Capillary Electrophoresis", *Analytical Chemistry*, 2001, 73(23), 5771-5775 [Abstract only—see p. 29 of CAPLUS search report].
Dong, Q. et al., "Monitoring Diclofenac Sodium in Single Human Erythrocytes Introduced by Electroporation Using Capillary Zone Electrophoresis with Electrochemical Detection", *Electrophoresis*, 2001, 22(13), 2786-2792 [Abstract only—see p. 30 of CAPLUS search report].
Widada, J. et al., Quantification of the Carbazole 1, 9a-Dioxygenase Gene by Real-time Competitive PCR combined with Co-Extraction of Internal Standards, *FEMS Microbiology Letters*, 2001, 202(1), 51-57 [Abstract only—see p. 32 of CAPLUS search report].
He, Y. et al., "Capillary-Based Fully Integrated and Automated System for Nanoliter Polymerase Chain Reaction Analysis Directly from Cheek Cells", *Journal of Chromatography*, 2001, 924(1-2), 271-284 [Abstract only—see p. 33 of CAPLUS search report].
Chen, S. et al., "Continuous Cell Introduction for the Analysis of Individual Cells by Capillary Electrophoresis", *Analytical Chemical Society*, 2001, 73(1), 111-118 [Abstract only—see p. 36 of CAPLUS search report].
Krylov, S.N. et al., "Instrumentation for Chemical Cytometry", *Analytical Chemistry*, 2000, 72(4), 872-877 [Abstract only—see p. 39 of CAPLUS search report].

Zhang, Y. et al., "Multiplexed Automated DNA Sequencing Directly from Single Bacterial Colonies", *Analytical Chemistry*, 1999, 71(22), 5018-5025 [Abstract only—see p. 40 of CAPLUS search report].

Becker, H. et al., "Multichannel Arrays on Polymer Substrates-towards a Disposable Proteomics Chip", *Proceedings of SPIE-The International Society for Optical Engineering*, 1999, Part 2, 728-733 [Abstract only—see p. 43 of CAPLUS search report].

Sims, C. E. et al., "Laser-Micropipet Combination for Single-Cell Analysis", *Analytical Chemistry*, 1998, 70(21), 4570-4577 [Abstract only—see p. 47 of CAPLUS search report].

Yang, L. et al., "Capillary Isoelectric Focusing-Electrospray Ionization Mass Spectrometry for Protein Characterization", *Book of Abstracts, 213$^{th}$ ACS National Meeting*, Apr. 13-17, 1997, American Chemical Society: Washington, DC [Abstract only—see p. 50 of CAPLUS search report].

Urbina, J.A. et al., "Antiproliferative Effects of Δ24(25) Sterol Methyl Transferase Inhibitors on Trypanosoma(Schizotrypanum) Cruzi: in Vitro and in Vivo Studies", *Chemotheraphy*, 1996, 42(4), 294-307 [Abstract only—see p. 51 of CAPLUS search report].

Herrmann, M. et al., "A Rapid and Simple Method for the Isolation of Apoptotic DNA Fragments", *Nucleic Acids Research*, 1994, 22(24), 5506-5507 [Abstract only—see p. 52 of CAPLUS search report].

Lewin, H.A. et al., "A Simple Method for DNA Extraction from Leukocytes for Use in PCR", *Biotechniques*, 1992, 13(4), 522, 524 [Abstract only—see p. 53 of CAPLUS search report].

Boado, R.J. et al., "A One-Step Procedure for Isolation of Poly(A) + mRNA from Isolated Brain Capillaries and Endothelial Cells in Culture", *Journal of Neurochemistry*, 1991, 57(6), 2136-2139 [Abstract only—see p. 54 of CAPLUS search report].

Zahn, R.K. et al., "Highly Protective Alkalinization by Ammonia Vapor Diffusion in Viscosimetric DNA Damage Assessment", *Analytical Biochemistry*, 1988, 168(2), 387-397 [Abstract only—see p. 55 of CAPLUS search report].

Liu, N., "Hydroxyapatite centrifugation method and its application in the study of DNA by radiation and its repair," *Shengwu Huaxue Yu Shengwu Wuli Jinzhan*, 1985, 61, 42-5 [Abstract only—see p. 56 of CAPLUS search report].

Lagrue, G. et al., "Serum Complement. Biochemical Properties and Method of Activation", *Nouvelle Presse Medicale*, 1973, 2(34), 2265-2270 [Abstract only—see p. 57 of CAPLUS search report].

Tan, M., "Isolation of Micronuclei from Euplotes Octocarinatus and Identification of an Internal Eliminated Sequence in the Micronuclear gene Encoding *y-tubulin 2", European Journal of Protistology*, 1999, 208-216 [Abstract only—see p. 66 of CAPLUS search report].

Baba, Y. et al., *Micro Total Analysis Systems: Proceedings of the μTAS Symposium*, Nov. 3-7, 2002, vol. 1 & 2, Kluwer Academic Publishers, Hingham, MA, ISBN: 1-4020-1011-7, (2003).

Houtoff, H. et al., "Platinum-containing Compounds, Methods for their Preparation and Applications Thereof", 1999, Kreatech Diagnostics: Netherlands.

Morbidity and Mortality Weekly Report, Atlanta, Ga., CDC:105.

* cited by examiner

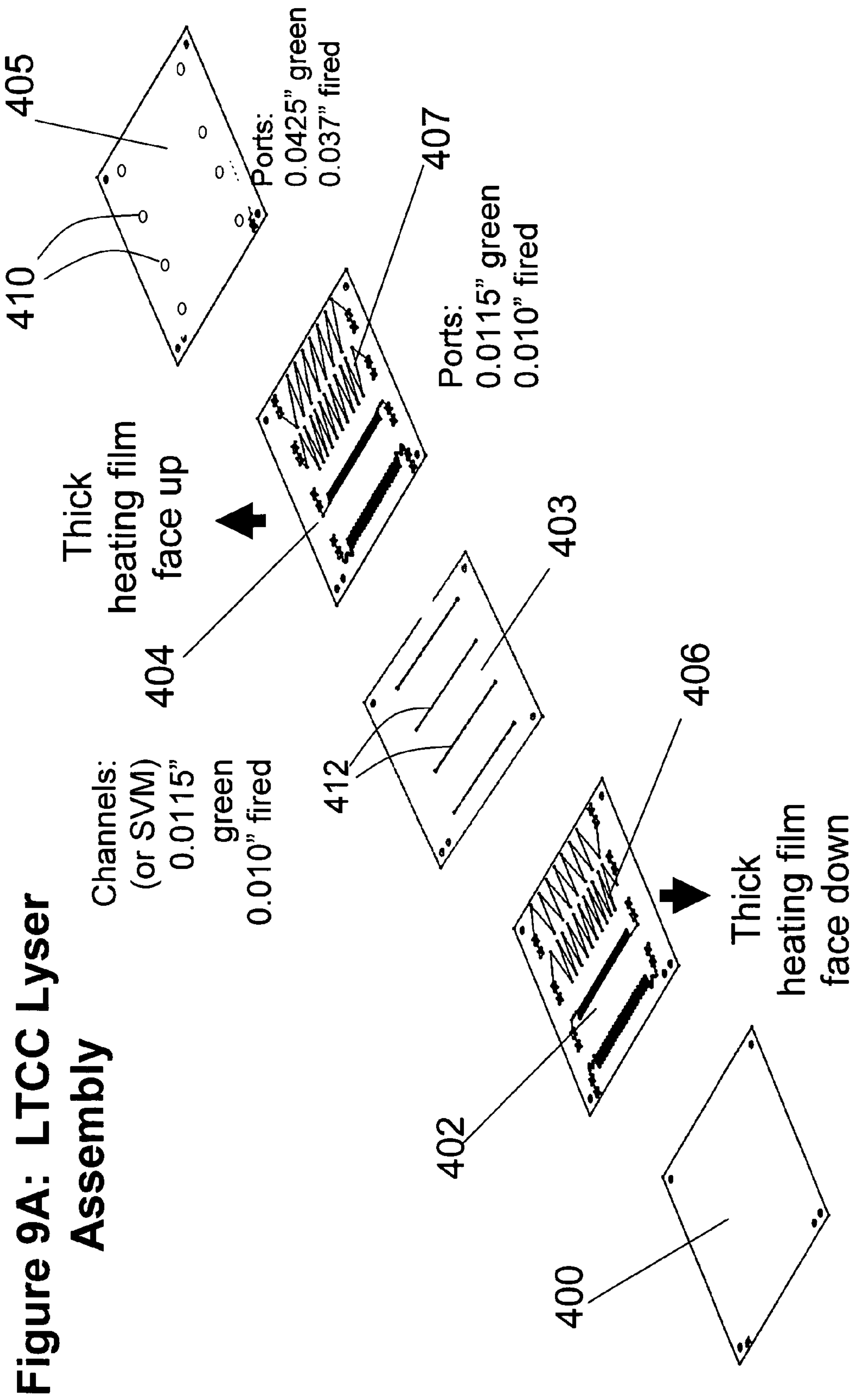
Figure 9A: LTCC Lyser Assembly

Figure 10 Temperature Response curve
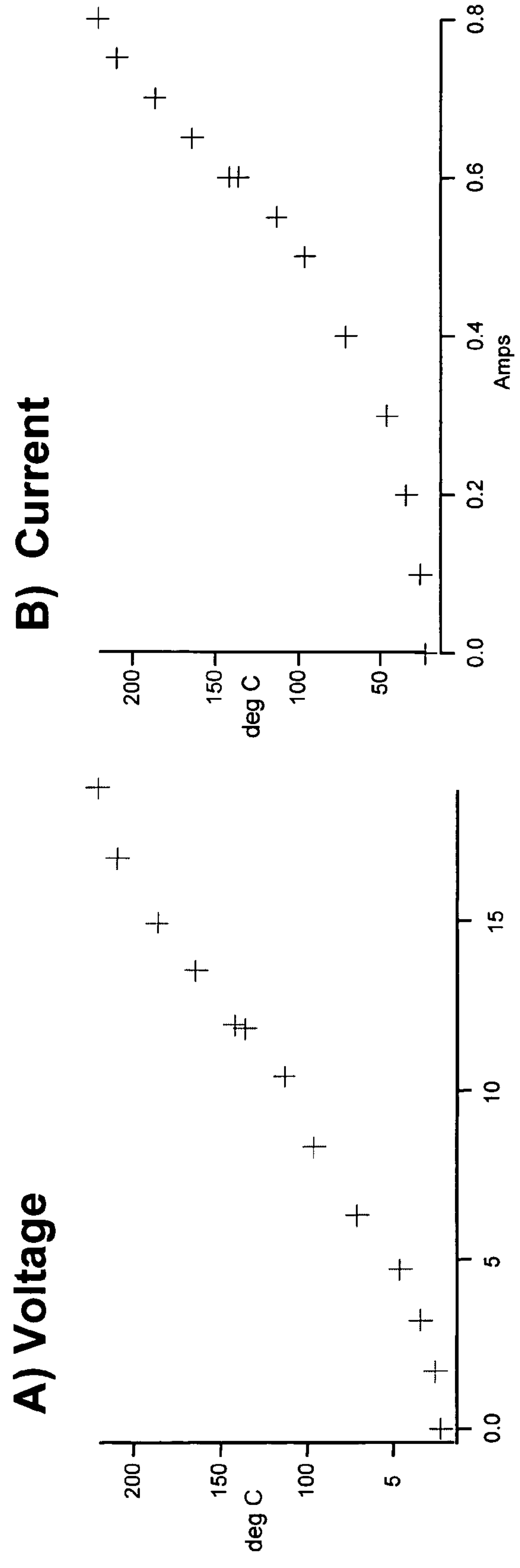

Figure 11 Ceramic Lyser with integrated heaters
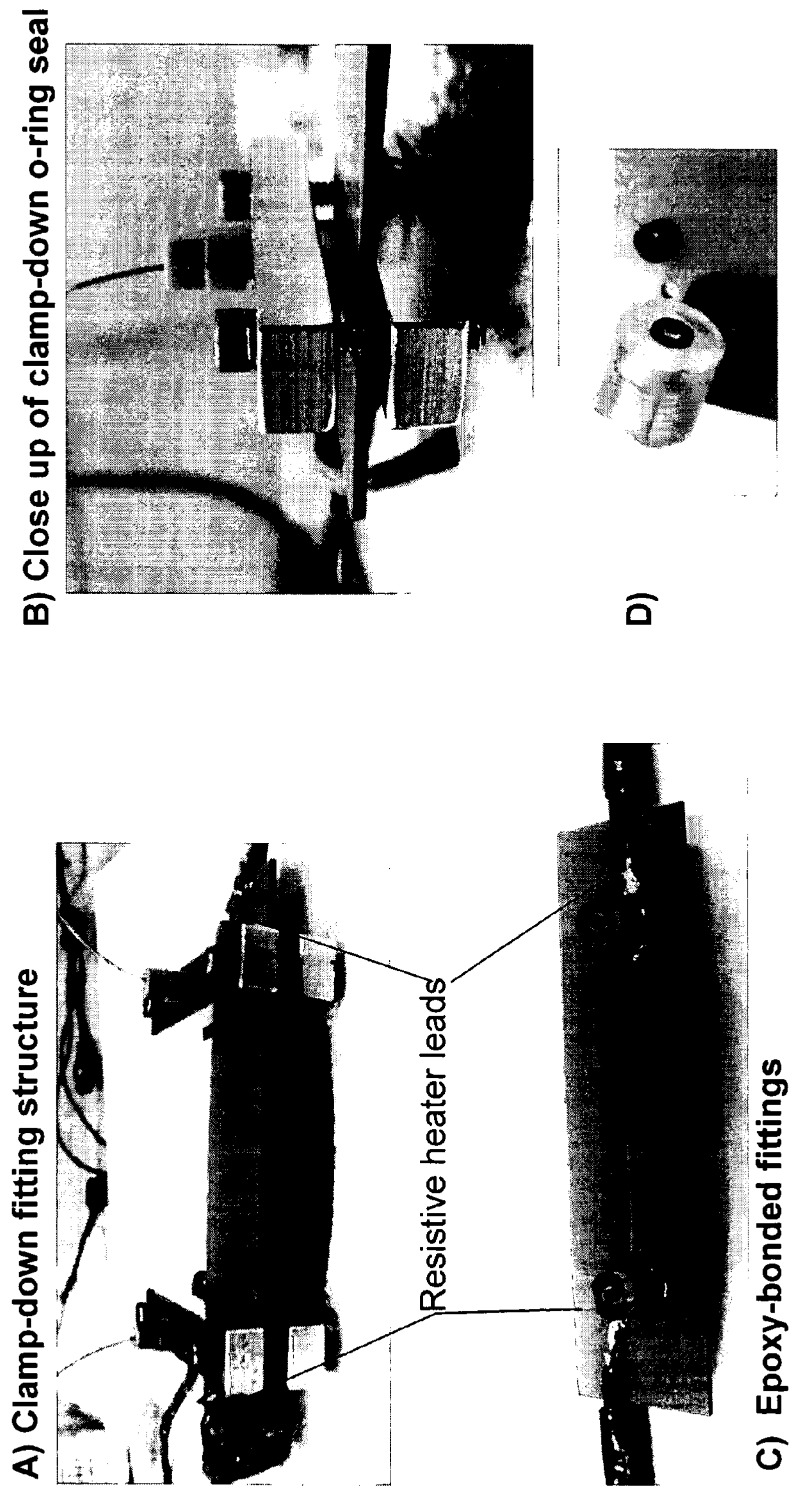

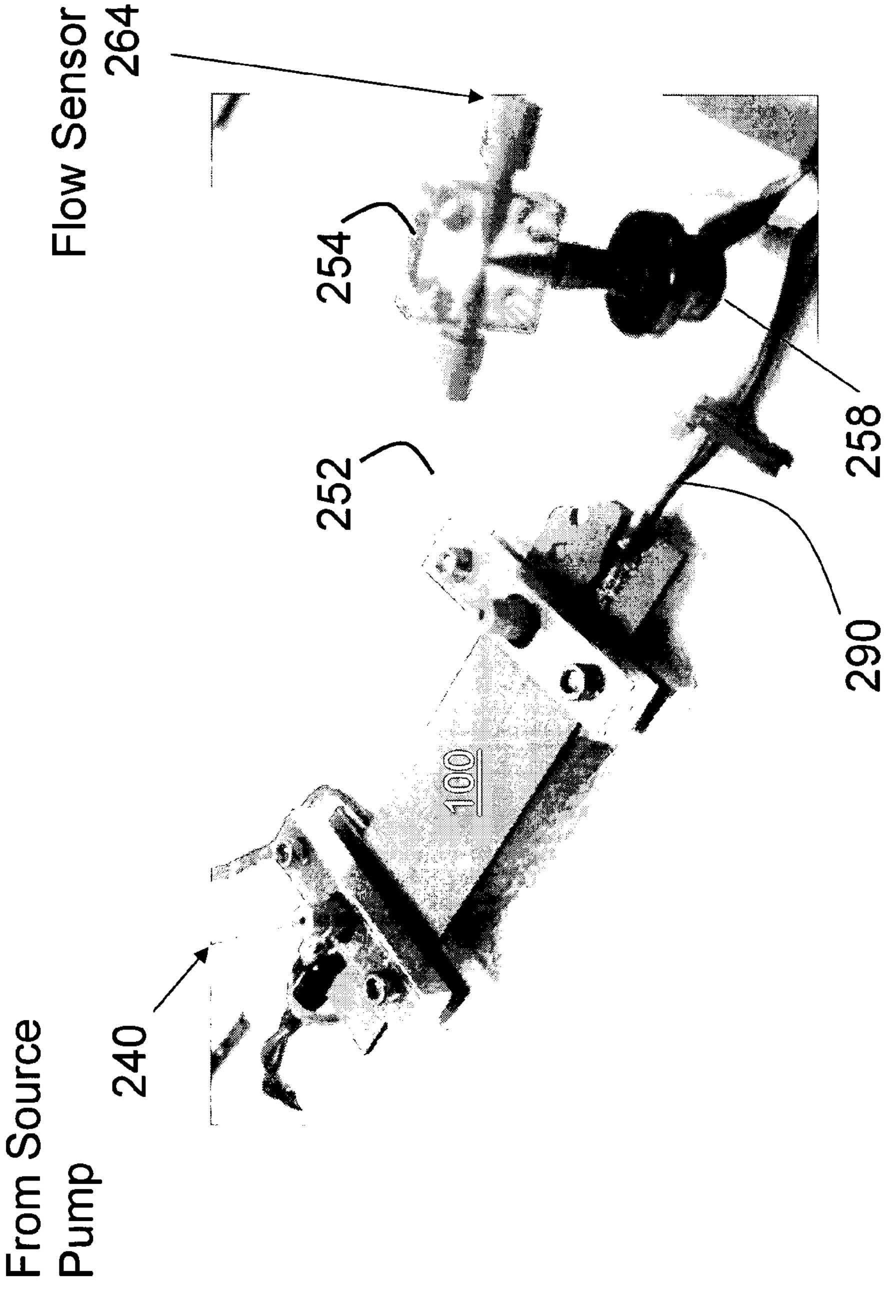
Figure 12 Ceramic Lyser setup with flow restrictor and pressure sensor Figure 13 Lyser Results for *Bacillus subtilis* spores
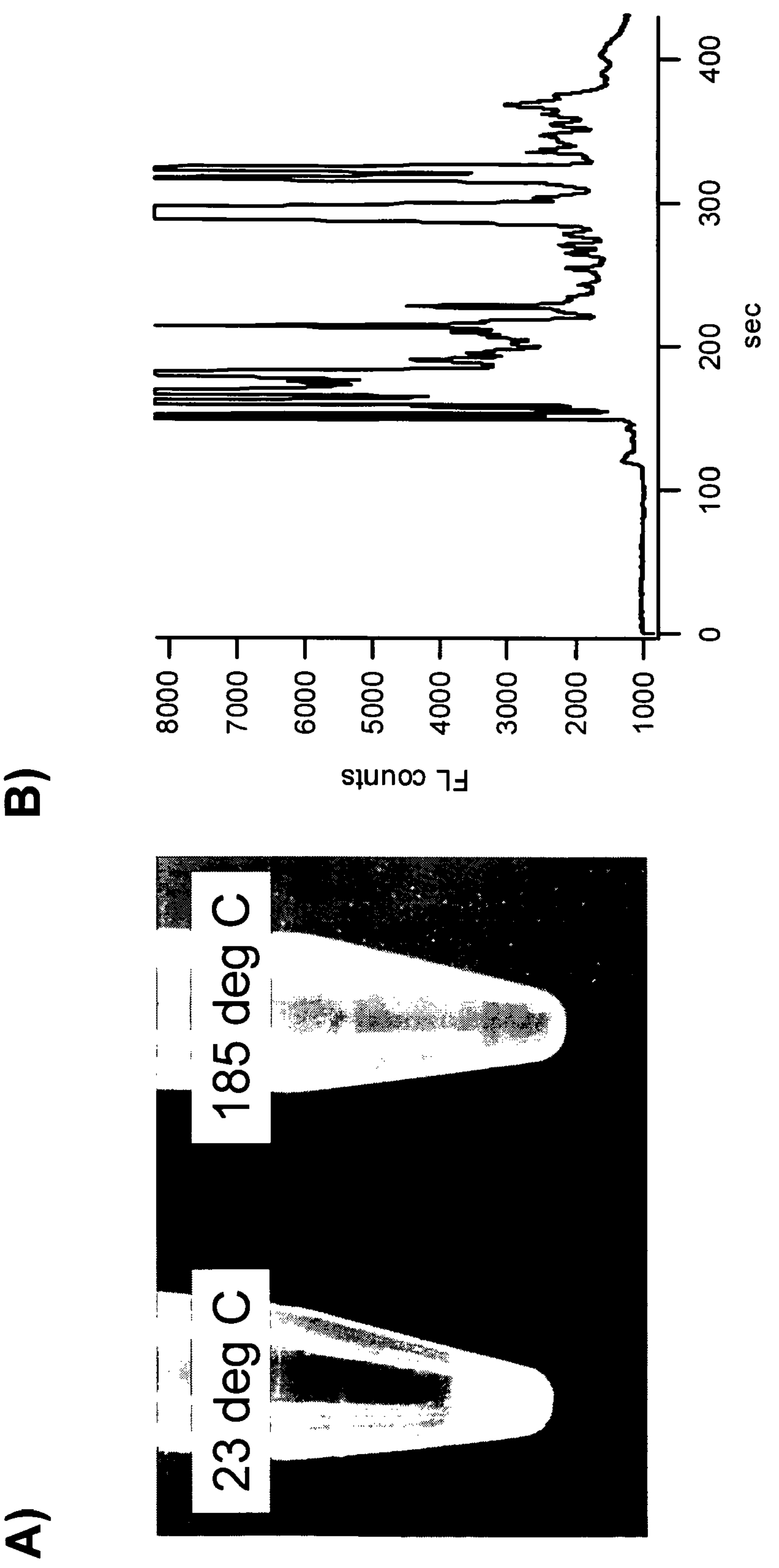

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial
<220> FEATURE:
<223> OTHER INFORMATION: Primer

<400> SEQUENCE: 1

gtttcgctcc                                                              10


<210> SEQ ID NO 2
<211> LENGTH: 10
<212> TYPE: DNA
<213> ORGANISM: Artificial
<220> FEATURE:
<223> OTHER INFORMATION: Primer

<400> SEQUENCE: 2

aagagcccgt                                                              10
```

HIGH TEMPERATURE FLOW-THROUGH DEVICE FOR RAPID SOLUBILIZATION AND ANALYSIS

CROSS-REFERENCE TO RELATED APPLICATIONS

This application claims benefit of U.S. Provisional Application No. 60/612,969, filed on Sep. 24, 2004, the entirety of which is incorporated by reference herein.

STATEMENT OF GOVERNMENT INTEREST

This invention was made with Government support under Government Contract No. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

FIELD OF THE INVENTION

The present invention is related to methods and devices for lysing cells. The present invention is also related to methods and devices for analyzing lysed cells.

BACKGROUND OF THE INVENTION

Field portable analysis of biological agents depends on the ability to prepare unknown samples for analysis. A major component of sample preparation is lysing and solubilizing biological agents. Sample preparation is complicated by the wide variability in the stability of biological agents to the effects of lysis and solubilization. A variety of techniques have been developed for lysing viruses and bacterial agents, examples of which include chemical and detergent lysis, enzyme treatment, sonication, heating, and glass bead milling. Bacterial spores, for example, are extremely resistant to lysis and solubilization, often requiring a combination of the aforementioned techniques. However, many of these lysis techniques complicate analysis due to the addition of chemical additives or proteins to the samples which interfere with the amplification, labeling or analytical analysis.

Several sample processing techniques have been developed for the use and integration of microfluidic devices. These techniques and microfluidic devices include integrated detergent mediated lysis, laser mediated cell lysing, and electric field mediated lysis. In addition, highly integrated systems have been developed that allow for the lysis, concentration, purification, and analysis of DNA from *E. coli*. Many of these studies perform sample processing on relatively labile eukaryotic cell types, and bacteria. Few studies have been directed to rapidly lysing and analyzing bacterial spores for microfluidic analysis. Belgrader, et al., ("A minisonicator to rapidly disrupt bacterial spores for DNA analysis," *Analytical Chemistry,* 71(19), 1999, 4232-6) previously demonstrated that sonication of *Bacillus subtilis* spores in the presence of silica beads was an effective technique for lysis prior to polymerase chain reaction ("PCR") analysis of spore DNA. Taylor, et al., ("Lysing bacterial spores by sonication through a flexible interface in a microfluidic system," *Analytical Chemistry,* 73(3), 2001, 492-6) followed up these studies by demonstrating real-time PCR and protein signature analysis using a similar device.

Sample preparation is complicated by the wide variability in the stability of biological agents to the effects of lysis and solubilization. Numerous techniques have been developed for lysing spores, viruses, and cells. Common examples include enzyme digestion, chemical reducing agents, sonication, heating, and glass bead milling. Bacterial spores are extremely resistant to lysing and require harsh conditions to solubilize. A common protocol is to use a reducing agent such as TCEP (tris(2-carboxyethyl)phosphine) or DTT (dithiothreitol). In order to further analyze the solubilized proteins, the reducing agent must be removed, a time-consuming and labor intensive step.

Thus, there is a continuing need to develop sample processing techniques useful for a variety of analytical techniques including protein fingerprinting and PCR. There is also a need to develop sample processing techniques useful for immunological based reagent detection and other electrophoretic analysis. In addition, there is a need to develop protocols to process extremely robust sample agents such as bacterial spores for direct integrated analysis using microfluidic devices for protein fingerprinting. There is also a need to develop devices that rapidly lyse bacterial spores for use in DNA analysis using, such as PCR, using microfluidic devices and chips.

SUMMARY OF THE INVENTION

The present invention provides processes that rapidly solubilize a wide variety of biological agents. These processes include a thermal solubilization protocol for bacterial spores using ethylene glycol, water, or any combination thereof, as a carrier solvent. The present invention also provides a flow through device (hereinafter "lyser") having the capability of performing flow-through high temperature lysis of biological materials such as cells from multicellular organisms as well as unicellular organisms (e.g. bacteria, bacterial spores and viruses). Lysers can be integrated with a sample preparation station for fluorescent dye labeling and sample buffer mixing with lysates of biological materials. Using these methods and devices, various biological agents, such as viruses, vegetative cells, and spores (e.g. *Bacillus anthrasis, Bacillus cereus*, and *Bacillus subtilis* spores), as well as bacteriophage viruses, can be solubilized and labeled to form elutants. This device can be coupled to a hand portable analysis platform for analysis and identification. The elutants generated from this process can be used for a variety of both protein and DNA analysis methods. The methods and devices of the present invention enable, among other things, rapid preparation of samples of viruses, bacteria and bacterial spores for protein fingerprint analysis using a miniaturized capillary electrophoresis ("CE") platform.

The present invention also provides for devices for lysing biological material, comprising an inner conduit for transporting the biological material, the inner conduit having an entrance and an exit; and a heater situated exterior to the inner conduit capable of heating the biological material to at least about 125° C.

The present invention also provides for systems for delivering biological material to an analytical device, comprising a biological material source; a thermal lyser comprising an entrance and an exit, the entrance being in fluid communication with the biological material source; a dye source in fluid communication with the exit of the thermal lyser; a buffer source in fluid communication with the exit of the thermal lyser; and an exit capable of being in fluid communication with the analytical device.

The present invention also provides for micro-Total Analysis Systems ("µTAS systems"), comprising an analytical device, and a system for delivering biological material to an analytical device, comprising a biological material source; a thermal lyser comprising an entrance and an exit, the entrance being in fluid communication with the biological material source; a dye source in fluid communication with the exit of the thermal lyser; a buffer source in fluid communication with the exit of the thermal lyser; and an exit capable of being in fluid communication with the analytical device.

The present invention also provides for methods of preparing a biological sample for analysis, comprising flowing a biological sample fluid comprising biological material and a solvent through a conduit; heating the biological sample fluid as it flows through said conduit to greater than 100° C. at a pressure greater than 1 atmosphere to lyse at least a portion of the biological material; and labeling at least a portion of the lysed biological material with a dye.

The present invention also provides for methods of preparing a biological sample for analysis, comprising flowing a biological sample fluid comprising biological material and a solvent; heating the biological sample fluid as it flows to a temperature greater than about 100° C. and a pressure greater than about 1 atmosphere.

The present invention also provides for methods of analyzing a biological sample, comprising flowing a biological sample fluid comprising a biological material and an solvent; heating the biological sample fluid to at least 100° C. as it flows; lysing at least a portion of the biological material to release biomolecules; labeling at least a portion of the biomolecules with a rapid reacting dye; and measuring the molecular distribution of the labeled biomolecules.

Other aspects of the present invention will be apparent to those skilled in the art in view of the detailed description and drawings of the invention as provided herein.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods, compositions, and devices disclosed. In the drawings:

FIG. 9A is an exploded view of an embodiment of a thermal lyser of the present invention.

FIG. 10A depicts a temperature versus voltage response curve for the thermal lyser depicted in FIG. 9A.

FIG. 10B depicts a temperature versus current response curve for the thermal lyser depicted in FIG. 9A.

FIGS. 11A-B are photographs of various views of an embodiment of a thermal lyser having clamp-down fittings.

FIGS. 11C-D are photographs of various views of an embodiment of a thermal lyser having bonded fittings.

FIG. 12 is a photograph of a sample preparation module of the present invention.

FIG. 13 depicts *Bacillus subtilis* spore lysing results using the thermal lyser depicted in FIGS. 11A-D.

DETAILED DESCRIPTION OF ILLUSTRATIVE EMBODIMENTS

Terms

Figure 1A:
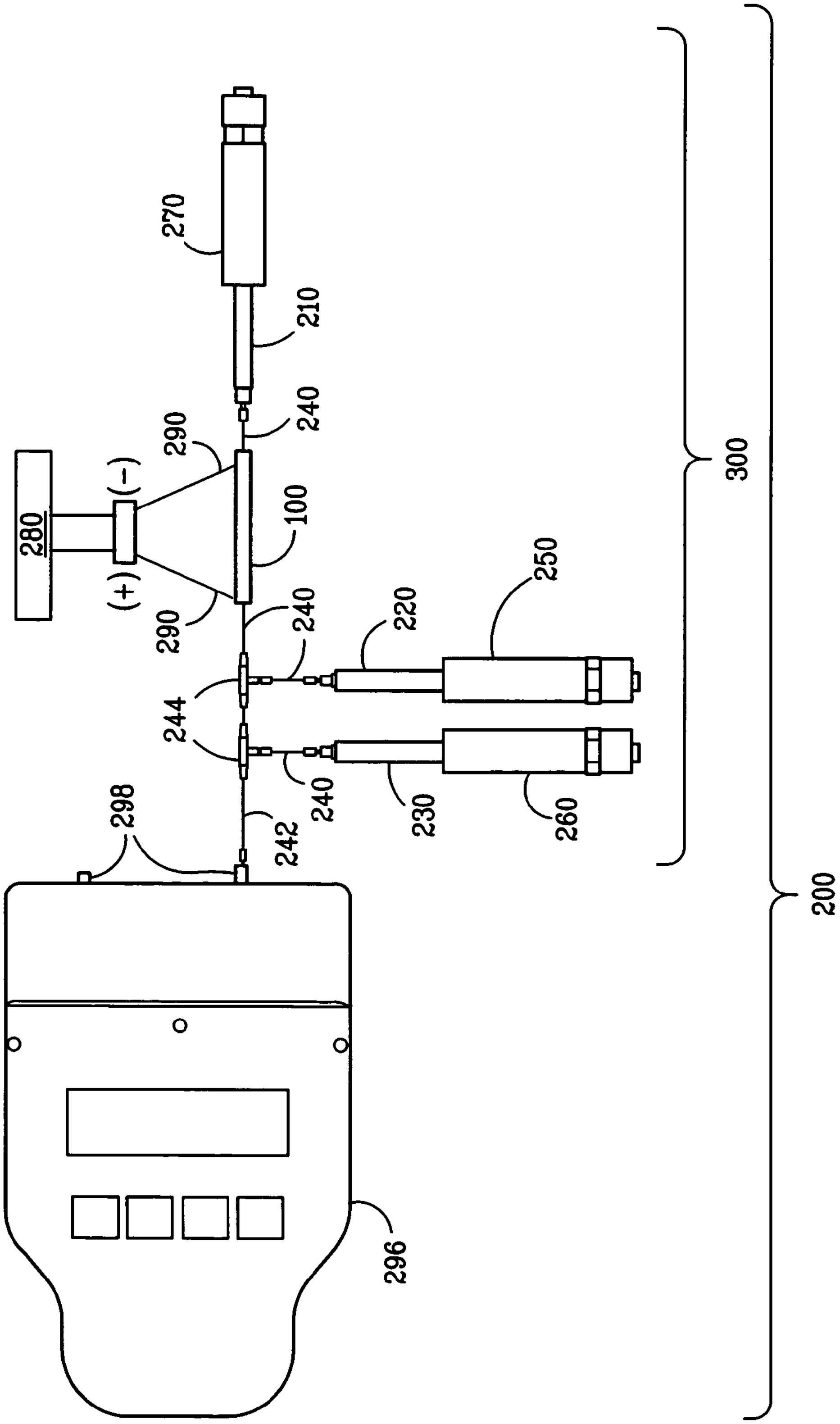
FIG. 1A is a schematic illustration of an embodiment of a system of the present invention.

As used herein, the term "to lyse" means to break open cells, cellular components, organelles, or any combination thereof to release biological molecules.

As used herein, the term "lysate" refers to the products of lysing biological material, for example, biological molecules.

As used herein, the term "microchannel" refers to conduits, for example channels, having a dimension smaller than about 1000 microns.

As used herein, the term "biological material" refers to matter originating in single-cell and multicellular organisms.

As used herein, the term "fluid state" refers to the physical state of matter that is capable of freely flowing, such as a liquid, gas, or supercritical fluid.

As used herein, the term "analysis" refers to a process for determining the identity or nature of molecular components or of an organism.

As used herein, the term "high concentration" refers to a composition comprising more 30 weight percent of a specified component based on weight of the composition.

As used herein, the term "thick film" describes a film that is applied by a method of printing, which historically has included, inter alia, screen printing, stenciling, and direct writing. Modern methods of printing films are also encompassed by this term, the methods including, inter alia, ink-jet printing, photolithography, micro- and nano-imprint lithography, chemical vapor deposition, and ion beam lithography. Accordingly, the term "thick film" is not used herein to restrict the dimensions of a film to any particular thickness.

The devices of the present invention for lysing biological material ("lysing device") include an inner conduit for transporting biological material, the inner conduit having an entrance and an exit, and a heater disposed exterior to the inner conduit for heating the biological material as it is transported through the inner conduit. Suitable inner conduits can have a wide variety of sizes and shapes. For example, the conduits can have lengths ranging from as short as 0.1 cm to as long as about 50 cm. Typically, the conduits have a length in the range of from about 1 cm to about 20 cm, and preferably the conduit lengths are in the range of from about 5 cm to about 15 cm in length. Suitable conduits can also have a variety of cross-sectional areas and shapes. For example, suitable cross-sectional areas of the inner conduits can include circles, semicircles, squares, rectangles, triangles, as well as regular and irregular polygons. Circles are suitably used, such as provided by capillary tubes. Suitable cross sectional areas of the inner conduits can range from as low as 10 microns to as high as 1000 microns, typically in the range of from about 50 microns to about 500 microns, and preferably in the range of from about 100 microns to about 250 microns. Suitable inner conduits having circular cross-sectional areas suitably have diameters from as low as about 100 microns up to about 2000 microns, typically in the range of from about 250 microns to about 1000 microns, and preferably in the range of from about 500 microns to about 750 microns. Suitable inner conduits can be made of almost any material that is capable of transporting biological material. Conduits are suitably prepared using capillary tubes, microfluidic devices, and laminated layered materials having a microchannel in an interior layer bounded by one or more additional layers. Examples of suitable inner conduit materials include, plastics, glasses, metals, ceramics and combinations thereof. Suitable inner conduit materials are typically capable of transporting aqueous and organic solvents at temperatures up to at least about 70° C., typically at least about 250° C., and preferably up to at least about 400° C., such a glass, ceramic and stainless steel. Other suitable materials capable of transporting aqueous and organic solvents at elevated temperatures include engineering plastics, for example PEEK.

In certain embodiments, a thermal lyser can be formed using one or more glass layers on a microfluidic chip. Multiple microfluidic processes (i.e., lysing, clean-up, and analysis) can be operated on a single microfluidic chip. In these embodiments, regions on the microfluidic chips for lysing are thermally separated (e.g., insulated) from the other microfluidic processes on the chip.

Examples of biological matter that can be lysed and analyzed using the devices, systems, and methods of the present invention include organs, tissues, cells, spores, organelles, molecular aggregates such as hybridized nucleic acids and aggregated proteins, single molecules, as well as portions thereof, and combinations thereof. For example, prokaryotic cells, eukaryotic cells and any combination thereof, can be included in the biological material, such as cells from microorganisms, animals and plants. In particular, the biological matter includes bacterial cells, bacterial spores, viruses, prions, eukaryotic cells (blood cells, tissue, white cells), bone marrow, bone, or any combination thereof. Suitable biological materials that can be transported in the inner conduit are provided in a fluid state. Biological materials can be suitably provided in a variety of fluid states, such as by dispersing in a suitable solvent. Suitable methods of dispersing biological materials include water, ethylene glycol, high boiling point solvents (i.e., PEG, PEO), and any combination thereof. In certain preferred embodiments, biological materials are suitably dispersed using pressurized water above about 100° C., more suitably above about 125° C., even more suitably above about 150° C., further suitably above about 175° C., and also above about 200° C. Elevated pressures are suitably used to increase the boiling point of the solvent, such as water. In certain embodiments, the lysing temperatures are suitably below the boiling point of the solution at the operating pressure. In other embodiments, the lysing temperatures are slightly above the boiling point of the solution at the operating pressure. Without being bound to a particular theory of operation, a slight amount of boiling may assist disruption of biological materials, such as tough spore coats. Compositions of water and water soluble high boiling point organic solvents, for example water and ethylene glycol, are also suitable at elevated temperatures and pressures. Almost any type of solvent can be used for dispersing the biological material. Suitable solvents for dispersing biological material include water and ethylene glycol. In addition, detergents (such as Triton X-100, sodium lauryl sulfate, NP-40, CHAPS, CHES), buffering reagents such as boric acid, sodium phosphate, TRIS, or any other buffer used to control pH of lysis solutions, and any combinations thereof can be added to the solvent. Preferred solvent components for dispersing biological material include water, polyethylene oxide (PEO"), polyethylene glycol ("PEG"), ethylene glycol, propylene glycol, or any combination thereof.

Suitable inner conduits will have at least one entrance for receiving the dispersed biological material for delivering lysed biological material. The entrance will typically be constructed to permit fluidic attachment to a suitable conduit capable of providing a source of biological material. For example, a suitable conduit can be a capillary tube for delivering the biological material from a sample syringe or vial to the entrance of the lysing device. Conduits can be fluidically coupled to the entrance of the lysing device by using a suitable coupler, such as Cap Tite™ fittings (Sandia National Laboratories), Upchurch fittings (Upchurch Scientific), epoxy, or any combination thereof.

Lysing of the biological material typically takes place within the inner conduit. Suitable inner conduits will have at least one exit for delivering the lysed biological material for delivering lysed biological material for further processing. Further processing can include delivery directly to a suitable analytical device, or into a fluidic junction where subsequent operations are performed on the biological material. Examples of a suitable fluidic junction includes a mixing tee, a valve, a cross or fitting with a plurality of connections at a single point, mixing container, injection assembly, injection valve, injection loop or any combination thereof. Examples of further processing operations include contacting the lysed biological material with a dye, a buffer, DNA or protein standards, fluorescent markers, enzymes for analyte protein digestion or enzymes for DNA processing (such as Taq polymerase) or restriction digestion in addition to reducing agents such as tris-(2-carboxyethyl)phosphine (TCEP) or β-mercaptoethanol (BME) dithiotheritol (DTT), tris-(2-cyanoethyl) phosphine or any combination thereof. The exit of the inner conduit may also be fluidically coupled in parallel or in series with a plurality of subsequent processing steps. Preferably, the exit is fluidically coupled to a dye source, for dying lysed biological molecules, and a buffer source for preparing the sample for analysis or post processing. The exit may also be fluidically coupled to pressure sensors, flow sensors, pressure regulators, flow restriction devices, or any combination thereof.

A heater is disposed exterior to the inner conduit for heating the biological material as it is transported through the inner conduit. Suitable heaters include a heating coil, such as a metal wire, wrapped around the inner conduit for resistively or inductively heating the biological material within the inner conduit. Suitable heaters also include metal heating traces disposed exterior to inner conduits formed using layered substrates. For example, a metal heating trace can be formed on a substrate to generate heat when a current is applied. This heating trace can be positioned in a layered system exterior to an inner conduit formed in an adjoining or neighboring substrate. Other suitable types of heaters and methods for heating the biological material within the inner conduit include laser induced heating, heated air, heated block, chemical heating, vibration, or any combination thereof. In certain embodiments, the heater is capable of heating the biological material to a temperature of at least about 195° C. In certain of these embodiments, a suitable heater includes an RF induction heater, or a resistive heater, such as coiled metal wire. In one embodiment, a coiled metal wire is wrapped around a glass capillary tube that is used as the inner conduit. In certain embodiments, the heater is exterior to the inner conduit, and in certain cross sections, when compared to the total thickness, the heater can be located close to the inner conduit, for example a distance of about 0.002 inches (about 50 microns) when a thin substrate is used. In other embodiments, the distance between the inner conduit and heater can even be less than 50 microns, for example 40 microns, or 20 microns, 10 microns, 5 microns, or even as low as about 1 micron, if the heater is printed on the side facing the inner conduit, but protected by another thin layer that has a thickness of less than 50 microns, for example 40 microns, or 20 microns, 10 microns, 5 microns, or even as low as about 1 micron. In other embodiments, the heater is adjacent to, or inside, the lumen of the inner conduit.

In certain embodiments, the lysing devices of the present invention further include an optional outer conduit that surrounds the inner conduit. As with the inner conduits, the optional outer conduits may include any cross-sectional area, cross-sectional shape, or length. The length of the optional outer conduit can be any length, but when present, it is typically about the same length or slightly shorter as that of the inner conduit. The optional outer conduit can be used for supplying a variety of functions, for example, providing structural rigidity to the lysing device, providing thermal insulation, providing electrical insulation, conducting the heat to the inner conduit (this is done so that the inner conduit can be easily replaced and reduce carry over from sample to sample), or any combination thereof. In certain embodiments, the optional outer conduit is a coil insulator, such as a primary insulator, for thermally insulating the heater, electrically insulating the heater, or both. In certain embodiments in which the optional outer conduit insulates the heater, the heater is typically positioned between the optional outer conduit and the inner conduit. In the case of insulation there would be three conduits, the inner for transporting the fluidic sample, the middle for giving rigidity and conducting heat and the outer for insulation and electrical isolation. In certain embodiments, a suitable insulator in an outer conduit may include an open space, for example an air gap. Open spaces may be added to the insulators described herein. Open spaces are particularly useful for insulating and cooling the fluid within the inner conduit.

In certain embodiments, the lysing device may further include one or more additional secondary insulators. In these embodiments, secondary insulators can surround the heater, for example, by residing exterior to the optional outer conduit, or by residing between the optional outer conduit and the heater. Typical secondary insulators provide further thermal insulation of the lysing device. Examples of suitable secondary insulation materials include glass, plastic, fiberglass, low heat conductive ceramic foam, and any combination thereof.

The present invention also provides systems for delivering biological material to an analytical device. Suitable systems include a biological material source for providing biological material to a thermal lyser. Suitable biological material sources include sample syringes and vials. Suitable biological material sources typically include a delivery device and a pumping mechanism, or source pump, for transporting biological material into a thermal lyser. Suitable delivery devices, pumping mechanisms, and source pumps are typically capable of delivering biological material into the thermal lyser at flow rates as low as 0.01 μl/min up to flow rates as high as 1 ml/min, and preferably at flow rates from about 1 μ/min up to about 60 μl/min. Suitable delivery devices, pumping mechanisms, and source pumps include a syringe pump, a stepper motor, gravity feed, air pressure, water pressure, electrokinetic ("EK") pumps, peristaltic pumps, or any combination thereof.

Suitable thermal lysers for use in the systems of the present invention include any of the thermal lysers described herein, as well other thermal lysers that include an entrance for receiving a biological material, the entrance being in fluid communication with the biological material source, and an exit for delivering lysed biological material to an analytical device of subsequent processing steps. In certain embodiments, the systems of the present invention also include a dye source in fluid communication with the exit of the thermal lyser, a buffer source in fluid communication with the exit of the thermal lyser, and a delivery conduit for delivering dyed, lysed, biological material to an analytical device. Suitable dyes include a dye capable of binding to at least a portion of the lysed biological material exiting the exit of the lysing device. Examples of suitable dyes include flourescamine, naphthalene-2,3-dicarboxaldehyde (NDA), o-phthaldialdehyde (OPA), 3-(4-carboxybenzoyl)quinoline-2-carboxaldehyde (CBQCA), 3-(2-furoyl)quinoline-2-carboxaldehyde (FQ), 4-amino-4'-benzamidostilbene-2,2'-disulfonic acid, disodium salt (MBDS), alexa fluor, or any combination thereof. Many dyes are commercially available from Molecular Probes, Inc., Eugene, Oreg. Suitable dye sources include containers, vials, syringes, flasks, and the like, for containing a suitable dye. A pumping device (e.g. "a pump"), such as a syringe pump, is typically provide to actuate flow of one or more of the post-processing fluids. In addition to dyes and buffers, other examples of post-processing fluids include secondary standards, pH adjustment, addition of detergent (SDS), chelators, other aqueous solvents, acids, bases, photoactive solutions such as scintillation cocktail, or any combination thereof. Typically, at least one of the biological material source, the fluorescent dye source and the buffer source are transported using a pumping device.

In certain embodiments of the system of the present invention, the delivery conduit is capable of being in fluid communication with an analytical device. Suitable delivery conduits can include fittings or connections for fluidic coupling to a suitable analytical device. For example, delivery conduits are typically connected to an analytical device using commercially available Cap Tite™ fittings, Upchurch fittings, or any combination thereof.

Any of a variety of analytical devices can be connected to the systems of the present invention for delivering lysed biological materials. Suitable analytical systems include, microchemical analytical systems, mass spectrometers, chromatographs, PCR, slab gel 1-D, 2-D electrophoresis, CE separations, electrochemical cells, fluorescence detectors, photo diode arrays, Rad/nuc detection, and any combinations thereof. Preferably, the systems are fluidically coupled to a microchemical analytical device, such as any one of the μChemLab™ microanalytical systems being developed by Sandia National Laboratories. Other suitable microanalytical devices that are commercially available or otherwise available in the art include microbore HPLC, HANNA (Cepheid), and RAPID (Idaho technologies).

The present invention also provides micro-Total Analysis Systems ("μTAS systems"), in which lysed biological materials are provide by lysing systems that fluidically couple to microchemical analytical devices. In these embodiments, various μTAS systems can be coupled directly to the lysing systems of the present invention. Suitable microchemical analytical devices are capable of analyzing biological materials using any of a variety of methods, for example, mass spectrometry, hybridization microarrays, UV-VIS spectrometry, chromatography, electrophoresis, fluorescence detection, electrochemical cell detection, rad/nuc detection, and any combination thereof.

The present invention also provides methods of preparing biological samples for analysis. These methods include the steps of flowing a biological sample fluid comprising biological material and an organic or aqueous solvent, heating the biological sample fluid as it flows, and labeling at least a portion of the biological material with a dye. Any of the above-mentioned biological materials can be analyzed according to these methods. As described further in the examples below, these methods are particularly suited for preparing bacterial cells, bacterial spores, viruses, or any combination thereof for analysis.

In certain embodiments, the analysis identifies patterns or signatures for identifying a biological or chemical entity. Suitable examples of this analysis are described in U.S. Ser. No. 10/795,549, filed Mar. 8, 2004, "Viral Identification by Generation and Detection of Protein Signatures," the portion of which pertaining to viral signature analysis is incorporated by reference herein. In other embodiments, the analysis can use a single entity (such as a PCR primer) that discriminates between close isoforms of pathogenic bacteria and a biologically nearest neighbor. In these embodiments, single or multiple primers can be used to identify a biological agent in question. Alternatively the variety of either specific could be used which are designed to identify specific regions in the agents chromosomal DNA.

Suitable biological sample fluids include a biological material in an organic or aqueous solvent. Almost any composition of biological material and organic solvent can be used to form a suitable biological sample fluid. The amount of biological material in the biological sample fluid can be as low as one spore in a fluid sample having a volume of from about 10 μl to 1 ml. The weight percent of biological material in the biological sample fluid can be as high as 50 percent. Typically, the weight percent of the biological material is in the range of from about 0.00000001 percent, up to about 10 percent, and preferably in the range of from about 0.00001 percent, up to about 1 percent. Although a variety of additional components may be included in the biological sample fluid, for example water, salts, buffers, and contaminants, in certain preferred embodiments the biological sample fluid consists essentially of biological material and a suitable organic solvent. In other embodiments, the biological sample fluid consists essentially of biological material, buffer and water. In certain preferred embodiments, the biological sample fluid contains a high concentration of organic solvent. In other embodiments, the biological sample contains a high concentration of water.

Organic solvents that are suitably used in certain embodiments of the present invention are typically characterized as being at least partially water soluble. As used herein, the term "at least partially water soluble" means that a composition of a suitable organic solvent and water will exist thermodynamically in a single fluid phase, for compositions typically having at least about 1 percent by weight water, more typically at least about 2 percent by weight water, further typically at least about 5 percent by weight water, and even further typically at least about 10 percent water. In certain embodiments, the organic solvent is completely water soluble such that a single fluid phase is provide for any combination of organic solvent and water at STP.

In certain embodiments, suitable organic solvents include functional groups capable of hydrogen bonding. Examples of functional groups capable of hydrogen bonding include hydroxyl groups, ester groups, carboxylic acid groups, amine groups, thiol groups, and any combination thereof. Groups capable of hydrogen bonding typically impart at least partial water solubility to an otherwise water-immiscible organic solvent. Examples of classes of suitable organic solvents include alcohols, alkane diols, polyols, esters, diesters, and any combination thereof. Additional functional groups known in the solvent art can also be included. Among the alkane glycols, in certain embodiments, alkane diols, such as ethylene glycol, are preferably used. Although a suitable organic solvent composition can include ethylene glycol and any other component, the organic solvent in certain preferred embodiments consists essentially of ethylene glycol. Other organic solvents that are suitably used include aniline, cyclohexanone, decahydronaphthalene (decalin), dicyclopentadiene:cyclopentadiene dimer, diethylene glycoldibutyl ether, dimethyl sulfoxide, glycerol, formamide, nitrobenzene, tetrahydronaphthalene (tetralin) and any combination thereof. Suitable organic solvents can have a wide range of normal boiling points, and typically have a normal boiling point greater than about 25° C., more typically greater than about 100° C., even more typically greater than about 200° C., and further typically greater than about 300° C. In certain preferred embodiments, the normal boiling point of the organic solvent is in the range of from about 100° C. up to about 400° C.

In various method embodiments of the present invention, the biological sample fluid is heated as it flows. The biological sample fluid can be heated to almost any temperature, typically to at least about 50° C., more typically to at least about 75° C., even more typically to at least about 100° C., even more typically to at least about 125° C., further typically to at least about 150° C., to at least about 175° C., and in certain embodiments up to about 200° C., and even higher. These temperatures, will depend, in part, on the boiling point of the particular solvent and the system pressure. The boiling point of the solvent will typically increase with pressure. Superatmospheric pressures (i.e., above 1 atm), organic solvents, or both, can be used in various embodiments for achieving operating temperatures above 100° C. In related embodiments, a pressure restriction is provided in fluidic communication with the inner conduit to reduce mass fluid movements that can occur at boiling temperatures. Accordingly, a suitable solvent and system pressure is selected that facilitates post processing as well as increases the boiling point of the sample fluid.

Various methods can be used for heating the biological sample fluid as it flows. Examples of heating methods include flowing the sample fluid through a suitable fluid flow device, such as a conduit or channel, while applying energy to the sample fluid. Other suitable methods include flowing the sample fluid over a surface, or through on open space, while applying energy to the sample fluid. Examples of energy that can be applied to the sample fluid include radiant energy, thermal conductive energy, thermal convective energy, magnetic inductive energy, radio-frequency energy (e.g. microwave energy or laser), chemical energy (e.g. chemical reactions), nuclear energy (e.g. fission or fusion processes), and any combinations thereof. Suitable conduits include capillaries, tubes, pipes, and enclosed channels and trenches, such as provided in microfluidics devices or layered constructions. The sample fluid can also flow over various types of surfaces while heating. In certain preferred embodiments, the biological sample fluid is heated using any one of the thermal lysing devices described herein.

In certain preferred embodiments, the biological sample fluid is resistively heated by flowing the fluid through a region that is heated using electrical current flowing through a conductive material having a finite resistance. The heat is typically applied to the sample fluid as it flows, for example, current to resistance heaters that generates heat can be directed to pass through a suitable fluid flow device. A preferred method of heating includes flowing the biological sample fluid through a capillary that is surrounded by a wire coil that has an electric current in the range of from as low as about 0.001 amps, up to as high as about 100 amps, typically in the range of from about 0.1 amps, up to about 10 amps, and preferably in the range of from about 0.5 amps up to about 2 amps.

In certain embodiments of the method of the present invention, at least a portion of the biological material is lysed to form a lysate. Without being bound by any particular theory of operation, the biological material in the biological sample fluid lyses under physico-chemical forces created by the combination of the solvent environment, cavitation, bubble formation, heat, or any combination thereof. Biological molecules that are released upon lysing include nucleic acids, carbohydrates, amino acids, proteins, peptides, DNA, RNA, or any combination thereof. Biological material typically includes water molecules, which typically become incorporated in the biological sample fluid. Although most lysates will be readily soluble in the biological sample fluid, certain lysate portions, such as hydrophobic components, may use additional steps to solubilize at least a portion of the lysate. Examples of additional steps for ensuring solubilization of the lysates include a suitable surfactant, such as SDS, which is typically included in the buffer, or any combination thereof. Lysate solubilization may also assisted using vigorous mixing, shear, heating in surfactant, cavitation, bead beating, boiling, degassing, or any combination thereof.

In certain embodiments, the methods of the present invention also include the step of labeling at least a portion of the biological material with a dye as it flows. Suitable dyes are fluorescent and can be covalently attached to at least one biological molecule in the portion of the biological material. Many suitable dyes are commercially available and include Alexa Fluor, bimanes, succinimidyl esters, maleimides, succinimidyl 3-(2-pyridyldithio)propionate (e.g., for thiol derivatization of an amine), Cisplatin based DNA dyes (Kreatech), iodoacetamides, methyl nromides, hydrazines, hydroxylamine, dichlorotriazines, and any combinations thereof. Preferred dyes include a rapid reacting dye, which has the following characteristics: fluorogenic, uncharged, low MW. Preferred dyes include fluorescamine, nano-orange, monobromobimane, monochlorobimane, naphthalene-2,3-dicarboxaldehyde (NDA), dialdehydes o-phthaldialdehyde, and any combinations thereof. Labeling of at least a portion of the biological material with a suitable dye is typically carried out by contacting a biological sample fluid comprising lysed biological material with a dye under conditions to give rise to covalent bonding of the dye to a biological molecule. Suitable labeling conditions include controlled pH (8.5-9.5 for fluorescamine). The dye and the biological molecules can be contacted by a variety of methods. For example, dyes and biological molecules residing in separate flow devices can be combined or mixed together into a common flow device.

In the methods of the present invention, the biological sample fluid can flow over almost any distance with a combination of any of the above-mentioned heating methods to provide lysate. In certain embodiments, the biological sample typically flows a distance while it is heated of less than about 100 cm, more typically less than about 60 cm, even more typically less than about 30 cm, further typically less than about 20 cm, and even more typically less than about 10 cm. A wide variety of flow geometries, flow rates, and temperatures can also be used to provide lysing conditions for production of lysate. Accordingly, a wide variety of residence times during which the biological sample fluid is subjected to the lysing conditions can be achieved. Residence times can be as low as about 1 second to as high as about 1800 seconds, typical residence times range from about 10 seconds to about 600 seconds, and preferred residence times range from about 20 seconds to about 90 seconds. In various embodiments, the residence time of the biological material during heating is at least about 10, 30, 50, 70, 90, 110, 130, 150, 200, 250 or even 300 seconds. Likewise, in various embodiments, the residence time of the biological material during heating is no more than about 10, 30, 50, 70, 90, 110, 130, 150, 200, 250 or even 300 seconds. In certain preferred embodiments, the biological material is quickly heated in ethylene glycol for less than about 90 seconds, cooled an then labeled with a rapid reacting dye such as fluorescamine, and diluted with an aqueous buffer.

In the methods of preparing biological samples for analysis, certain embodiments of the present invention may include one or more additional processing steps. Examples of additional processing steps include polymerase chain reaction ("PCR"), solid phase extraction ("SPE"), dielectrophoresis, filtration, restriction digestion of DNA (for fragment analysis), trypsin digestion of proteins for mass spectrometry, and any combination thereof. In embodiments that include PCR, the concentration of organic solvent present during the PCR step is typically less than about 3 percent, preferably less than about 2.8 percent based on volume. PCR can be carried out by performing degenerate PCR on the lysate generated from the ultra-high temperature solubilization process. PCR analysis can be performed using a commercially available PCR kit, such as the Ready-To-Go™ RAPD analysis kit from Amersham Biosciences. Examples of PCR analysis conditions are as follows: each 25 ul reaction includes buffer (50 mM KCl, 1.5 mM $MgCl_2$ and 10 mM Tris-HCl, pH 9.0), 200 μM of each dNTP, (dATP, dCTP, dGTP, dTTP), and 1 to 1.5 units of Taq DNA Polymerase. A first reaction is carried out using a lysate diluted 1:16 in buffer. PCR is performed on this sample along with a series of further dilutions (1:1.3, 1:2, 1:4, and 1:20). Two sets of PCR are carried out, one using primer (5'-d [GTTTCGCTCC]-3') (SEQ. ID N0.1) and the other using primer (5'-d[AAGAGCCCGT]-3') (SEQ. ID NO. 2). Products are visualized on a 2% agarose E-Gel from Invitrogen. A second reaction is carried out on less concentrated dilutions of spores which are prepared prior to the sample lysing process. Low spore concentrated lysates are then prepared for analysis using the using the same post lysis dilution step used in the prior reactions. Spore dilutions include 1:2, 1:20, 1:200, and 1:2000. Dilutions of each lysate are used in the PCR (dilutions include 1:1.3, 1:2, 1:4, and 1:20). Primer 2 is chosen for this analysis. Products can also be visualized on a 2% agarose E-Gel from Invitrogen.

PCR processes can be incorporated, for example, by adding target specific primers to a solution that contains a lysate generated from a super-heated solubilization protocol (e.g., heating to a temperature above the normal boiling point of the solvent and under pressure to prevent boiling). For example, a solution is prepared containing water, 10× amplification buffer with 15 mM $MgCl_2$ which includes 10 mM dNTP, 50 μM oligonucleotide primer 1, 50 μM oligonucleotide primer 2, 5 unit/μl Taq Polymerase. A template DNA (Lysate) (1 μg genomic DNA, 0.1-1 ng plasmid DNA) in 10 μl is added to this solution. Reactants can be added in the following order for each reaction (on ice) in a 0.2 or 0.5 ml tube: 10×PCR buffer-10 μl, Primer 1-1 μl, Primer 2-1 μl, dNTP-2 μl, template DNA and water-85.5 μl, Taq Polymerase-0.5 μl. A control reaction is prepared with no template DNA and an additional 10 μl of sterile water. Sample vials or tubes are placed in a thermal cycler preheated to 94° C., and the following repeated program is performed: 1) 94° C. 1 min, 55° C. 1 min, 72° C. 1 min, for 30 cycles. A final extension at 72° C. for 7 min is performed. The products can be purified using a DNA extraction kit, such as QIAquick PCR Purification Kit available from Qiagen, Germantown, Md., then analyzed for size using an agarose gel.

Real-time PCR processes can be incorporated, for example, by adding target specific fluorescent primers to a solution that contains the lysate generated from the super-heated solubilization protocol. Briefly, using normalized primer concentrations and mixed gene-specific forward and reverse primer pairs, each primer (forward or reverse) should be in solution at an approximate concentration 5 pmol/μl. The following protocol can be executed on a real-time PCR instrument, such as an ABI Prism SDS 7000. In optically clear reaction vial add a mixture containing fluorescent dye, target DNA, primer pairs, and water. The following thermocycling protocol can be used to execute the PCR reaction: 1) 50° C. 2 min, 1 cycle, 2) 95° C. 10 min, 1 cycle, 3) 95° C. 15 s→60° C., 30 s→72° C. 30 s; repeated for 40 cycles, 4) 72° C. 10 min, 1 cycle. After thermocycling the products can be checked on an agarose gel (2-3%) and/or used for dissociation curve analysis.

Microarray processes can be incorporated, for example, by utilizing a fluorescent dye on to the DNA or RNA that is released from the lysed biological agents. This can be suitably performed, for example, by directly labeling the nucleic acids using a covalent linking dye or by performing cDNA synthesis step using an appropriate protocol based on the nature of the target material. Once the fluorescent dye is incorporated into target nucleic acids, they can be purified using a PCR clean-up kit, such as the QIAquick PCR Purification Kit. After purification the probes are diluted in a hybridization buffer containing 1-5×SSC (depending on protocol), 10-50% formamide, 0.1% SDS, 0.1-1% BSA and/or Cot-1 DNA for blocking non-specific binding. The solution is then added to pre-hybridized prepared microarray slide, incubated for 12-14 hours, then washed and imaged to determine the presence or absence of the specific gene sequences.

Alternatively, as described in U.S. patent application Ser. No. 10/701,097, filed Nov. 4, 2003, "Microfluidic Integrated Microarrays for Biological Detection," labeled nucleic acids can be transported to a microfluidic chip which contains a monolithic trapping polymer. The monolithic trapping polymer specifically isolates the labeled target nucleic acids. The trapped nucleic acids can then be washed and eluted directly onto a high density microfluidic gene array for analysis of the presence or absence of specific nucleotide sequences. The monolithic trapping polymer and microfluidic gene array may be situated on separate microfluidic chips, but preferably they are situated on the same microfluidic chip.

The present invention also provides methods of analyzing biological samples. These methods are capable of determining, for example, the composition of a biological sample in terms of protein, amino acids, DNA, mRNA, oligonucleotides, polysaccharides, or any combination thereof. Such determinations can be correlated to a compositional database for identifying the origin of the sample, whether having a natural origin (e.g. an organism such as a bacteria or virus), an unnatural origin (e.g. a synthetic compound or genetically-engineering organism), or a combination of both.

In certain embodiments, methods of analyzing biological samples include the steps of flowing a biological sample fluid comprising a biological material and an organic or aqueous solvent through a conduit, heating the biological sample fluid to at least 100° C. as it flows through the conduit, lysing at least a portion of the biological material to release biomolecules, labeling at least a portion of the biomolecules with a rapid reacting dye, and measuring the molecular distribution of the labeled biomolecules. The steps of flowing, heating, lysing, and labeling can be carried out in any of the ways described above. The step of measuring the molecular distribution can be carried out using a macromolecular analytical methodology that gives rise to a measurement of the molecular distribution. Examples of molecular distributions include molecular weight distribution, composition distribution, nucleic acid distribution, amino acid distribution, and any combination thereof. Measurement of any of these molecular distributions can be used for identifying the biomolecules, the source of the biomolecules, whether natural or unnatural, or any combination thereof. Suitable methods for determining molecular distribution can be carried using one or more chromatographic methods. Particularly preferred chromatographic methods can be carried out using microfluidics systems, such as those provided in U.S. Ser. No. 10/795,549, "Viral Identification by Generation and Detection of Protein Signatures", filed Mar. 8, 2004, which is incorporated by reference herein. One embodiment uses capillary electrophoresis to measure the molecular weight distribution. For example, rapid cell lysis can be performed using a flow-through lysing apparatus as provided herein to heat a flowing ethylene glycol containing solution to as high as 195° C. The flow-through lysing apparatus can be constructed by wrapping a 0.5 mm diameter copper wire around a 10 cm 450/640 ID/OD capillary glass (Polymicro Technologies, Phoenix, Ariz.) fused silica capillary with approximately 20 windings/ cm. A second capillary (150 i.d./360 o.d.) can be inserted into the heating capillary to provide sample flow through the heating element, which enables the heating of one or more capillaries using a single heating device. The external windings can be insulated using a fiberglass insulation webbing and soldered to a simple two prong connector for operation using a standard 10V power supply. Induction heating can be performed using an applied field of 1.6 volts with 0.6-1.6 Amp ("A") current. Internal temperature of the capillary during induction heating can be measured using a 0.1 mm diameter platinum wire inserted into the inner capillary connected to a thermocouple interface. Thermocouple interfaces are commercially available from Fluka.

Bacteria, spores and viral samples can be pelleted by centrifugation and resuspended in a buffer containing 5 mM boric acid, 5 mM SDS dissolved in 98% ethylene glycol. Samples are then transferred to a syringe connected to a 150/360 capillary for flowing though the thermal lyser using a syringe pump. Real time imaging of cell lysis for bacteria and spores can be performed using a light microscope to observe both inlet and outlet capillaries. Spore lyses is confirmed by counting spore particles imaged between two glass slides before and after lysing.

Microchannel gel electrophoresis analysis of the lysed agents can be performed using a thermal lyser that is connected to a second sample preparation station that adds dye and buffer to the sample stream. For example, 10 mM fluorescamine dye in acetonitrile and an electrophoresis buffer (composed of 5 mM boric acid/5 mM SDS dropwise adjusted to pH 8.6 with 1N NaOH) can be added to the sample stream. The flow rate is preferably selected to achieve about a 5% lysed sample/10% fluorescamine dye solution/85% electrophoresis buffer. This solution is then pumped directly in a hand-portable microchannel electrophoresis instrument to perform microchannel gel electrophoresis of the prepared sample.

Examples and Additional Embodiments

Fluorescent dyes 8-hydroxypyrene-1,3,6-trisulfonic acid (HPTS)(ex 405/em 510 nm) and fluorescamine (ex 395/em 475 nm) were obtained from Molecular Probes (Eugene, Oreg.). Ethylene glycol boric acid, sodium dodecyl sulfate (SDS), $\alpha$-lactalbumin (14.4 kDa), carbonic anhydrase (32.5 kDa), ovalbumin (45 kDa), bovine serum albumin (66 kDa) were purchased from Sigma (St. Louis, Mo.). Mouse IgG (147 kDa) was obtained from Transduction Laboratories (San Jose, Calif.). Cholecystikinin flanking peptide (CCK) is a synthetic peptide (1.1 kDa) obtained from Commonwealth Biotechnologies (Richmond, Va.). Polyethylene glycol/polyethylene oxide sieving gel, in the 14-200 kDa range (part # 477-416), was purchased from Beckman (Fullerton, Calif.). All other chemicals purchased were reagent grade or better.

Bacterial growth and spore production. Preparation of *Bacillus* spores was performed as has been previously described (Nicholson, et al., *Sporulation, Germination and Outgrowth, in Molecular Biology Methods for Bacillus*, C. R. Harwood and S. M. Cutting, Editors, 1990, John Wiley & Sons Ltd, New York, pp. 391-450). Initial growth for cultures took place in Luria-Bertani media (20 g/L, LB Broth, Difco). Small scale cultures incubated overnight at 37° C. were diluted and used to inoculate large scale cultures at an O.D. of 0.05 at 600 nm. When cultures reached an O.D. between 0.4 and 0.6 at 600 nm, cells were spun down for 10 minutes in a centrifuge at 5,000 g's and then re-suspended in an equal volume of a sporulation media. The sporulation media used herein consisted of 1.0 ml of 0.1 M CaCl2 (autoclaved), 4.0 ml of 5% L-glutamate (pH 7.0 with 10 M NaOH, filter sterilized), 4.0 ml of 1 M MgSO4.7$H_2O$ (autoclaved), and 90 ml of sporulation salts (3.3 μM FeCl3.6$H_2O$, 40.1 μM MgCl2.6$H_2O$, 100 μM MnCl2.4$H_2O$, 0.01 M NH4Cl, 75 μM Na2SO4, 50 μM KH2PO4, 1.21×10−3 M NH4NO3) per 100 ml. Cultures remained incubated at 37° C. for 48 hours. Samples were centrifuged at 10,000×g and the supernatant decanted. Purification included 3 washes with sterile dH2O, 1 wash with 1 M KCl/0.5 M NaCl, 1 wash with 1 M NaCl, 1 wash with 2 M NaCl, 1 wash with 0.25% SDS, and 3 washes with sterile d$H_2O$. All washes occurred in ¼ the original culture volume with centrifugation at 10,000×g for 10 minutes. Purified spores were then re-suspended in sterile d$H_2O$ and stored at 4° C.

T-even bacteriophage growth and purification. Phages were produced by the multi-cycle lysis-inhibition technique described by Doermann et al., ("Genetic control of capsid length in bacteriophage T4. Isolation and preliminary description of four new mutants," *Journal of Virology*, 12(2), 1973, 374-85, the entirety of which is incorporated by reference herein). An overnight culture of the appropriate host strain was diluted 1:100 into 1 L medium M103 (medium M9 plus 1% casamino acids) and incubated at 37° C. with aeration until the cell density reached $4\times10^8$ colony-forming units ("cfu")/per milliliter ("mL"). The culture was shifted to 30° C. and cells were infected at a MOI of 0.1 plaque-forming units ("pfu") per cfu. Incubation continued at 30° C. for 180 minutes post-infection when pregnant bacteria were harvested by centrifugation and re-suspended in 50 mL of buffer BUM (13.3 g/L $NA_2HPO_4$ 7HOH, 4 g/L NaCl, 3 g/L $KH_2PO_4$ and 1 mM $MgSO_4$). Cells were lysed by vortexing in the presence of $CHCl_3$. Cellular debris was removed by centrifugation at 3000×g for 15 minutes. Phages were pelleted by centrifugation at 18,000 g's for 1 hour. Phage pellets were covered with 25 mL of 2-amino-N,3,3-trimethylbutanamide ("BUM") buffer and stored overnight at 4° C. prior to re-suspension by gentle mixing. The integrity and purity of these viral preparations were confirmed by transmission electron microscopy.

System for Rapid Cell Lysing and Analysis. Referring to FIG. 1A, rapid cell lysis was performed using sample preparation module 300 and analysis was carried out using analytical device 296, which was fluidically coupled to thermal lyser 100. The combination of sample preparation module 300 and analytical device 296 is system 200. The thermal lyser 100 used in this embodiment is capable of heating a flowing organic or aqueous solution to temperatures as high as 195° C. The thermal lyser 100 has resistive electrical leads 290 that are connected to power supply 280. The thermal lyser 100 receives sample fluid through a conduit 240, which receives sample fluid from biological material source 210 (shown here as a syringe). The biological material source 210 flows upon activation of source pump 270. Sample fluid is heated within the thermal lyser 100, and the cells are at least partially lysed. Lysed cells exit the thermal lyser 100 and pass through fluidic junctions 244 that are separately connected to a dye source 220 pumped using dye pump 250, and buffer source 230 using buffer pump 260. Lysed, dyed and buffered samples exit the sample preparation module 300 at delivery conduit 242, where it enters the analytical device 296 through one of the sample inlet ports 298.

Figure 1B:
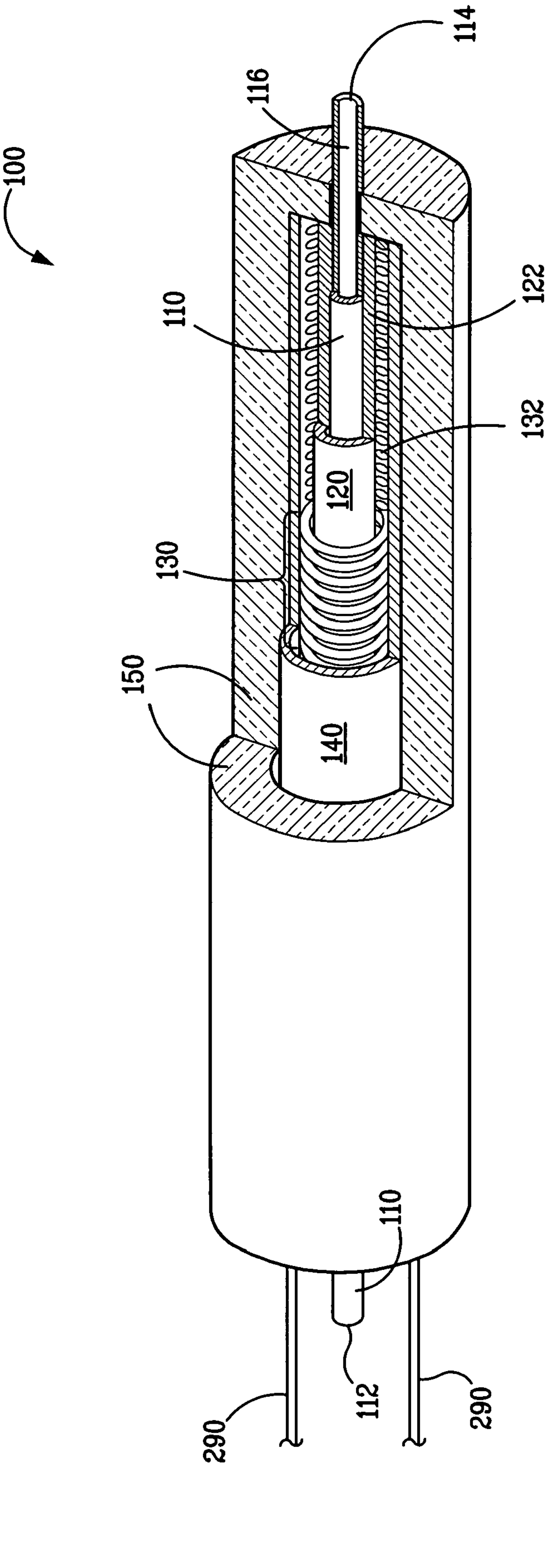
FIG. 1B is a cut-away schematic illustration of an embodiment of a lysing device of the present invention.
Figure 1C:
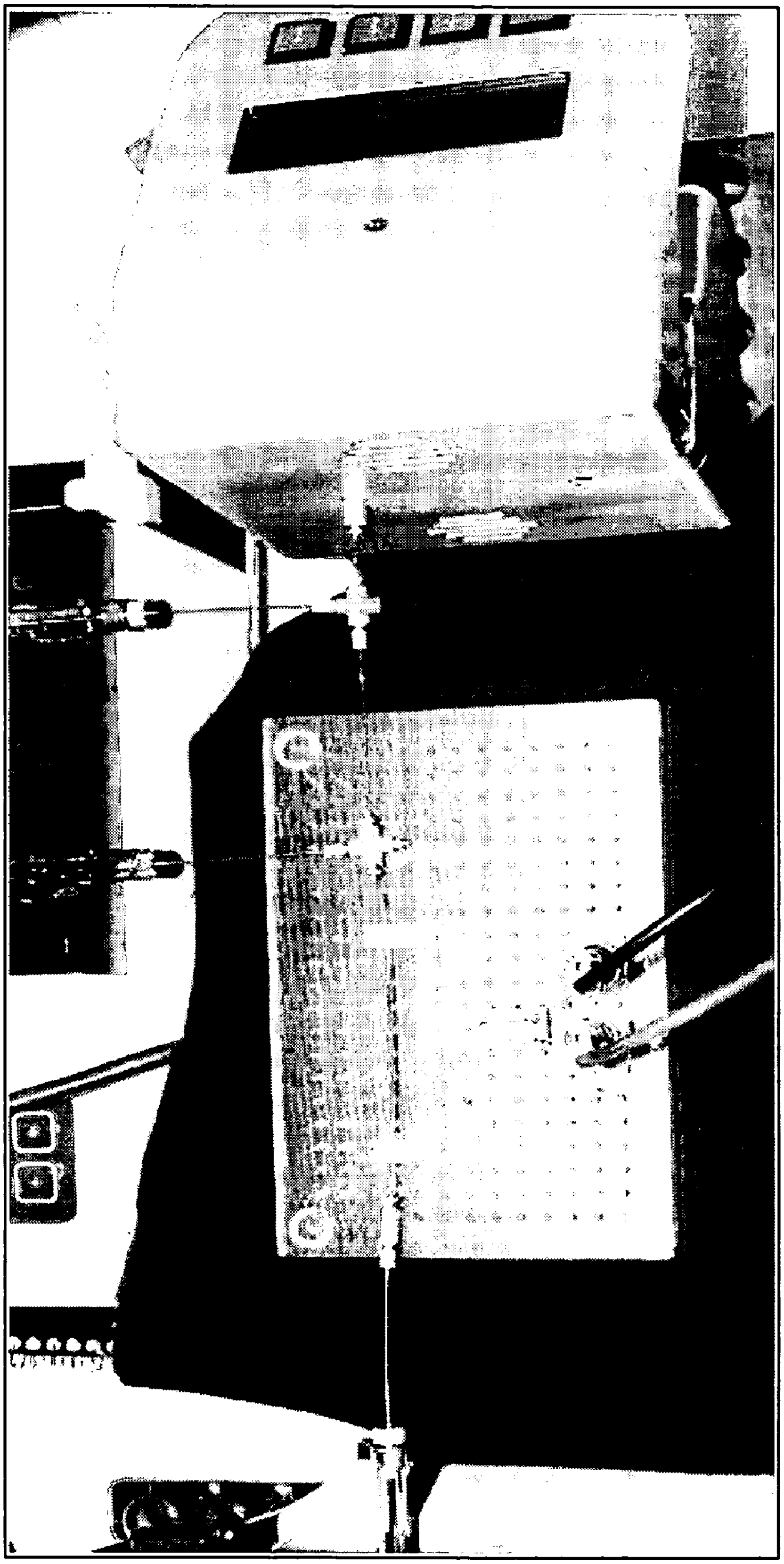
FIG. 1C is a photograph of an embodiment of the system of the present invention.

Referring to FIG. 1B, thermal lyser 100 was constructed by providing a heater 130 by wrapping a 0.5 mm diameter copper wire 132 around a center portion 5 cm of a 10 cm long nominal 450 μm I.D.×640 μm O.D. glass outer capillary 120 (hereinafter "450/640 capillary") obtained from Polymicro Technologies, LLC (Phoenix, Ariz.) with approximately 20 windings/cm. An inner conduit 110 (a second capillary, nominally 150 μm I.D.×360 μm O.D., hereinafter "150/360 capillary" or "inner capillary") was inserted into the outer conduit 120 (a capillary) to provide sample flow through the heater 130. This design enables the use of one or more capillaries with a single heater (only one inner conduit is shown inserted in the outer 120). The heater 130 (resistive heating coil wire 132 surrounding outer conduit 120) was enclosed using a primary insulator 140 (a layer of fiberglass insulation webbing in this example) to control the temperature within the inner capillary 110. The coil wire ends were soldered to a two prong connector (not shown) for use with a standard 10V power supply 280 (shown in FIG. 1A). Resistive heating was performed using an applied current of about 1.5V with 0.6-1.6 A current. Internal temperature of the inner capillary during heating was measured using a small diameter copper-indium wire (not shown) inserted into the capillary containing ethylene glycol and connected to a thermocouple interface (e.g., a potentiometer, not shown).

Bacterial, spores and viral samples were pelleted by centrifugation and re-suspended in a buffer containing 5 mM boric acid, 5 mM sodium dodecyl sulfate ("SDS") dissolved in 98% ethylene glycol. Samples were then transferred to a syringe connected to a 150/360 capillary used to pumped though the thermal lyser using a syringe pump. Real time imaging of the cell lysis for bacteria and spores was performed using a light microscope to set up to observe both inlet and outlet capillaries. Spore lysing was confirmed by counting spore particles imaged between two glass slides. Inactivation of the viable spores was also determined using standard colony growth procedures.

To perform microchannel gel electrophoresis analysis of the lysed agents, the thermal lyser was connected to a second sample preparation station which added fluorescamine dye in acetonitrile and an electrophoresis buffer (5 mM boric acid/5 mM SDS drop-wise adjusted to pH 8.6 with 1N NaOH) to the sample stream. The flow rate was set up to achieve a 5% lysed sample/10% fluorescamine dye solution/85% electrophoresis buffer. This solution was pumped directly into an analytical device (a hand-portable microchannel electrophoresis instrument described in U.S. Ser. No. 10/795,549, "Viral Identification by Generation and Detection of Protein Signatures", filed Mar. 8, 2004, the portion of which describing analytical devices is incorporated by reference herein, Renzi, R. F., et al., "Hand-portable analytical instrument for re-usable chip-based electrophoresis Part1: system design and integration", *Analytical Chemistry,* 77(2); (2005), pp. 435-441) to perform microchannel gel electrophoresis of lysed biological samples.

Separations were performed using 2.0-cm×2.0-cm fused-silica microfluidic chips fabricated from Corning 7980 fused silica wafers and obtained from Sensor Prep Services (Elbum, Ill.) using standard wet-etch procedures that are described in U.S. Ser. No. 10/795,549. These microfluidic chips contained a 10 cm separation microchannel which was filled with commercially available protein sieving gel for protein analysis. All channels were flushed with filtered deionized water and evacuated to dryness using a syringe connected to a capillary to a flush port on the microfluidic chip. This process was repeated three times. The microfluidic chip was filled with the sieving gel using a gas-tight, 250-μL syringe connected to the flush port. Channels were filled by applying modest pressure (~110 cm Hg) to the syringe for approximately 1-3 minutes.

In the analytical device buffers were contained in reservoirs connected to a manifold by a capillary-septum interface, as described previously in U.S. Ser. No. 10/795,549. The sample waste, buffer, and waste reservoirs were each filled with approximately 0.75 ml of sieving gel. The sample reservoir was filled with approximately 0.2 ml of sample buffer (5-mM boric acid and 5-mM SDS titrated with 1.0-M NaOH to pH 8.8). The liquid reservoir cartridge was installed on the fluidic manifold and the electrode plate was connected to the top of the fluidic reservoir cartridge. The injection currents/voltages were programmed using a user interface.

Sample preparation and electrophoresis. Samples were injected electrophoretically into the separation column as previous described in U.S. Ser. No. 10/795,549 with some alterations. Control of the sample plug on-chip was assisted by maintaining the current on the buffer leg between 0.2-0.6 μA. This protocol reduced variability in the current flow between the sample and sample waste channels. Separations were carried out using a constant current of 11.0 μA (@~450V/cm) on the waste leg. Sample and sample-waste voltages were chosen to reduce sample carryover and prevent sample leakage into the separation microchannel during a run. Laser-induced fluorescence detection was performed using a epifluorescent (EX 405 nm/EM 475 nm) optics module that was previously described. Data related to detected peaks were routed through an A/D converter and saved on a memory board for later analysis or viewed directly using a serial port connected to a laptop computer.

Data sets presented herein were uncorrected unless indicated otherwise. Corrected data were analyzed using a data analysis software package that subtracts out background noise and detects peak with a 3:1 ratio to the corrected baseline noise.

Figure 2A:
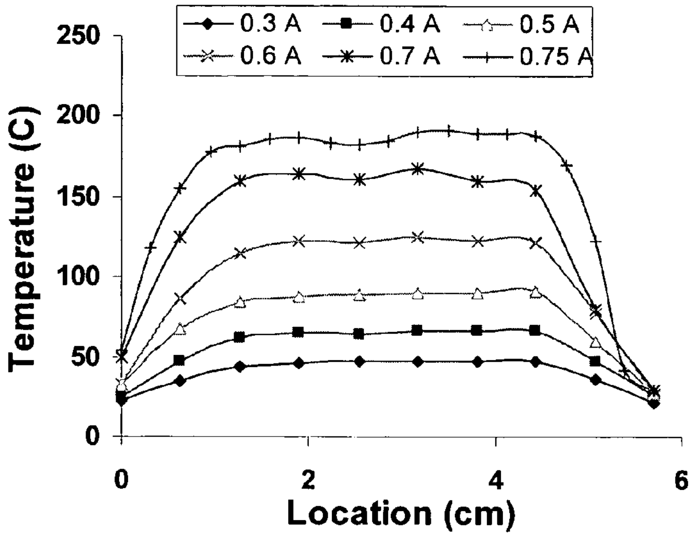
FIG. 2A illustrates the temperature of an ethylene glycol solution contained within the thermal lyser illustrated in FIG. 1B at various input current levels. Temperatures up to 195° C. across most of the interior of the lyser capillary are demonstrated.
Figure 2B:
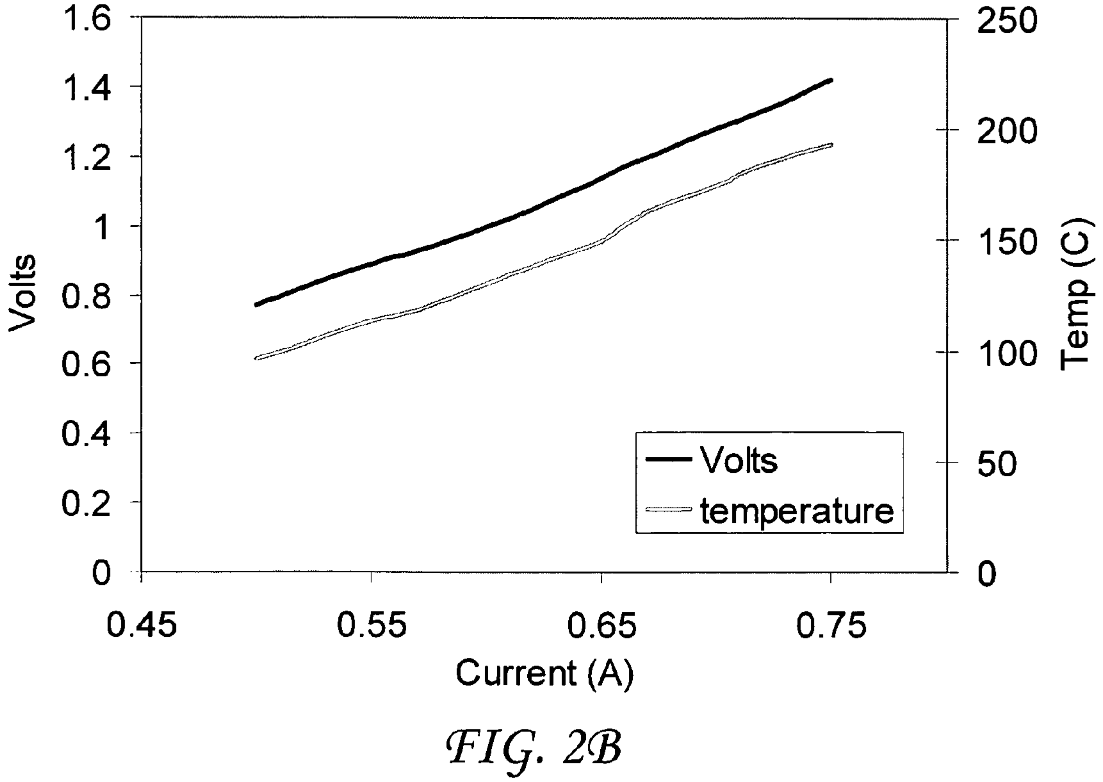
FIG. 2B depicts the relationships between current, voltage, and temperature within a lysing device of the present invention as fluid passes through the capillary at flows rates as high as 30 μl/min.

Implementation of an embodiment. A thermal lyser was routinely capable of rapidly heating solutions, such as ethylene glycol, up to temperatures as high as 195° C. The temperature remained generally constant across the length of the heating coil (FIG. 2A). Moreover, heating the capillary demonstrated a linear relation between current and applied voltage and temperature of the flow solution within the capillary (FIG. 2B). This enabled an accurate determination of the internal temperature with either applied voltage or current. The measurements of the internal temperature of the solution (shown in FIG. 2A) showed that the maximum temperature was achieved in the device within the first 0.5 cm of the 10 cm inner capillary and cooled to room temperature within 0.5 cm of exiting the portion of the capillary surrounded by the heating coil (FIG. 2A). Quick cooling to room temperature helped integrate the thermal lyser 100 into a complete sample preparation module (300, FIG. 1A) to perform sample labeling at room temperature (about 24° C.).

The thermal lyser 100, when performing at flow rates as a high as 30 μL/min, was also capable of elevating the temperature of the solution up to about 195° C. This flow rate gives rise to the appropriate residence time in the superheated solution which adequately lyses spores. Such flow rates advantageously decrease the overall time for sample processing.

Figure 3B:
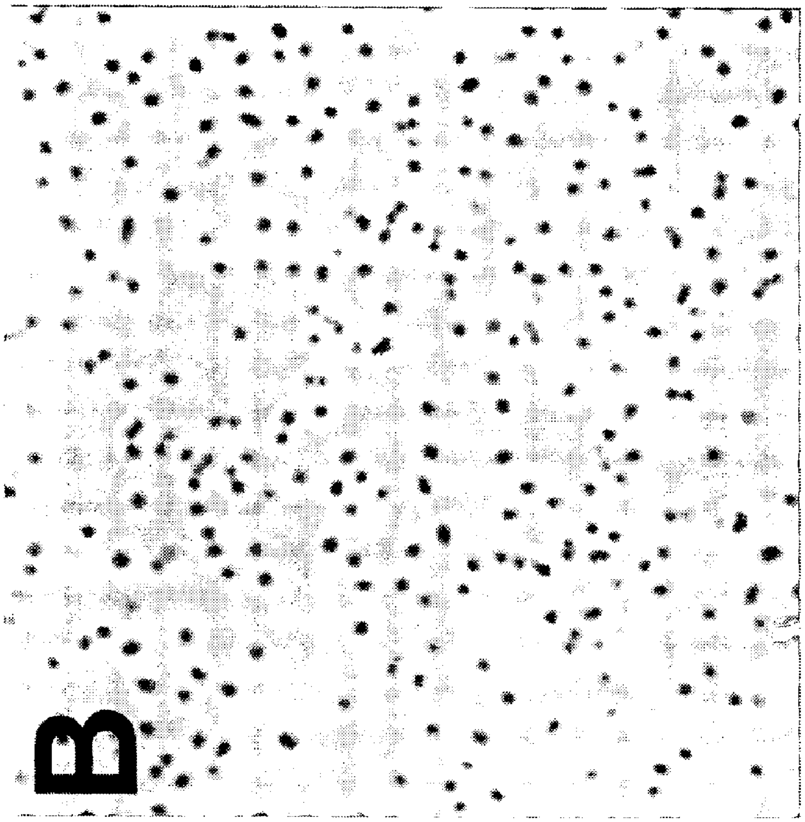
FIGS. 3A and 3B show spore particles of *Bacillus subtilis* prior to lysis using an embodiment of the lysing device and method of the present invention. The spore particles are imaged between two glass slides.
Figure 3A:
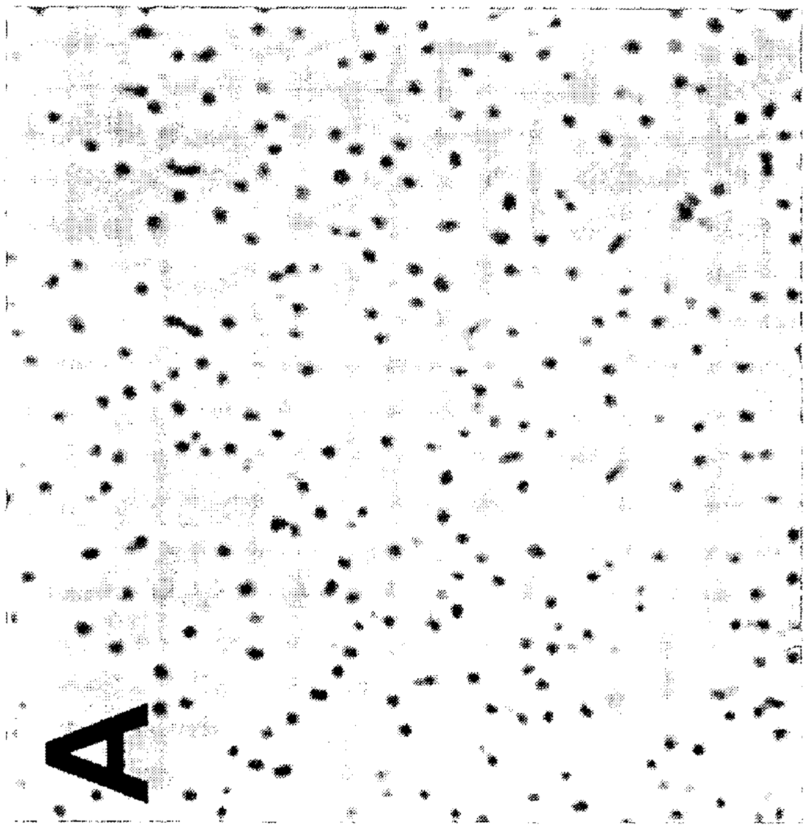
Figure 3D:
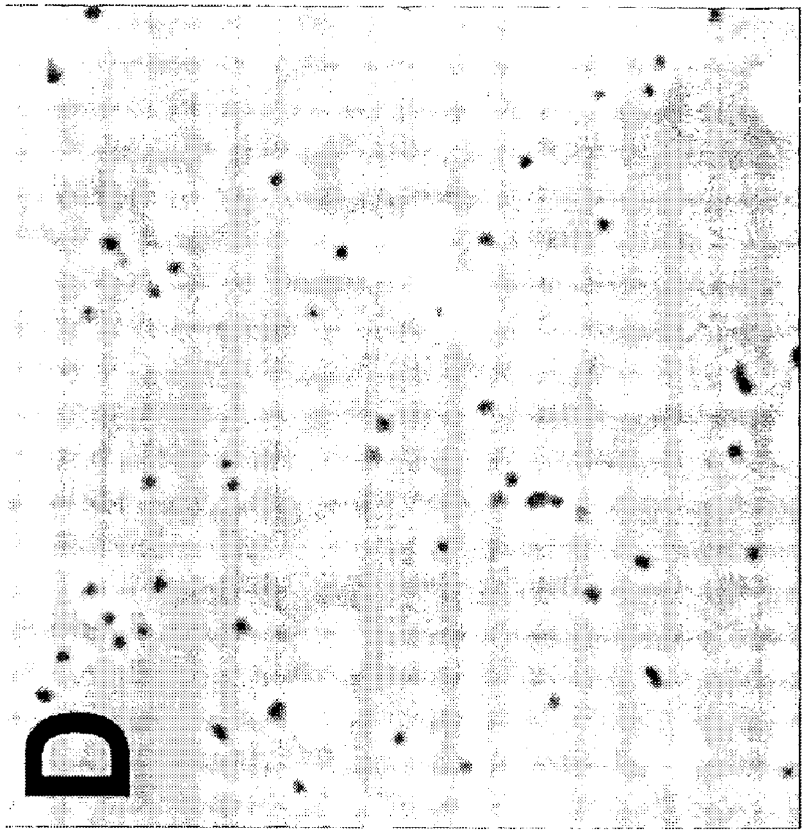
FIGS. 3C and 3D shows an approximate 80% reduction of the spore particles of *Bacillus subtilis* following lysis using an embodiment of the lysing device and method of the present invention.
Figure 3C:
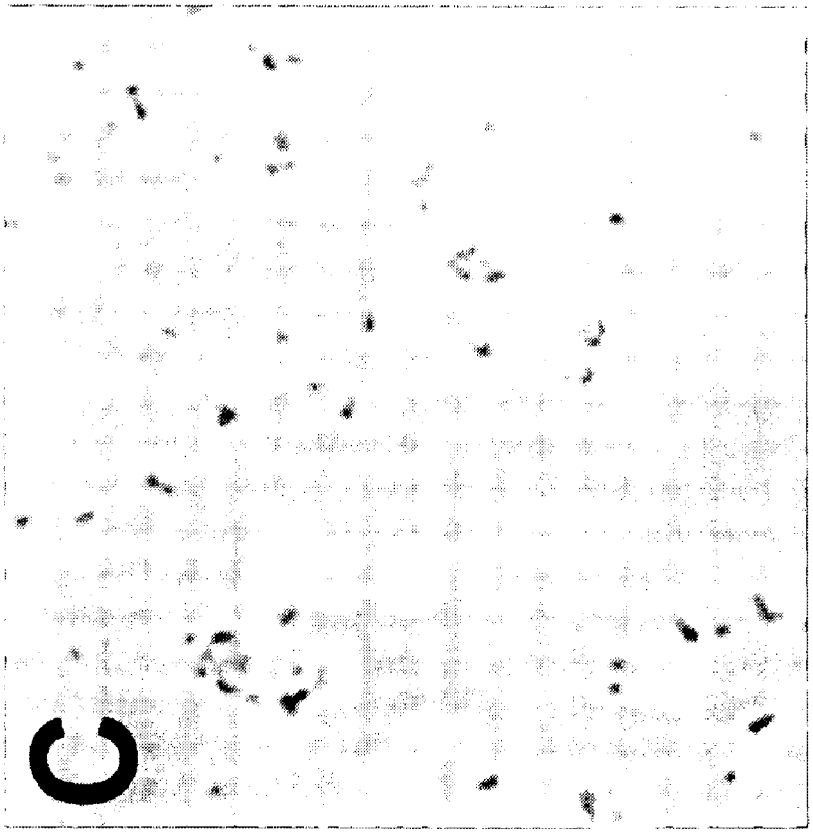

In several examples, thermal lysers as short as 5.0 cm were capable of achieving the necessary residence time for nearly complete bacterial spore solubilization. This was supported by the fact that these preparations were completely inactivated as judged by plaque forming analysis. Many *Bacillus subtilis* colonies submitted to the lysis procedures as described herein resulted in a reduction in the colony forming units ("cfu's"). Flow rates as high 6.0 μL/min provided adequate residence times (90 sec.) for spore solubilization. Imaging these spores demonstrated that the observable spore particles were reduced (FIGS. 3A-B) by greater that 80 percent following lysis (FIGS. 3C-D). Measured DNA was undetectable prior to spore lysis. In contrast, recoverable DNA concentrations as a 1 μg/ml after purification of spore lysates.

Figure 1D:
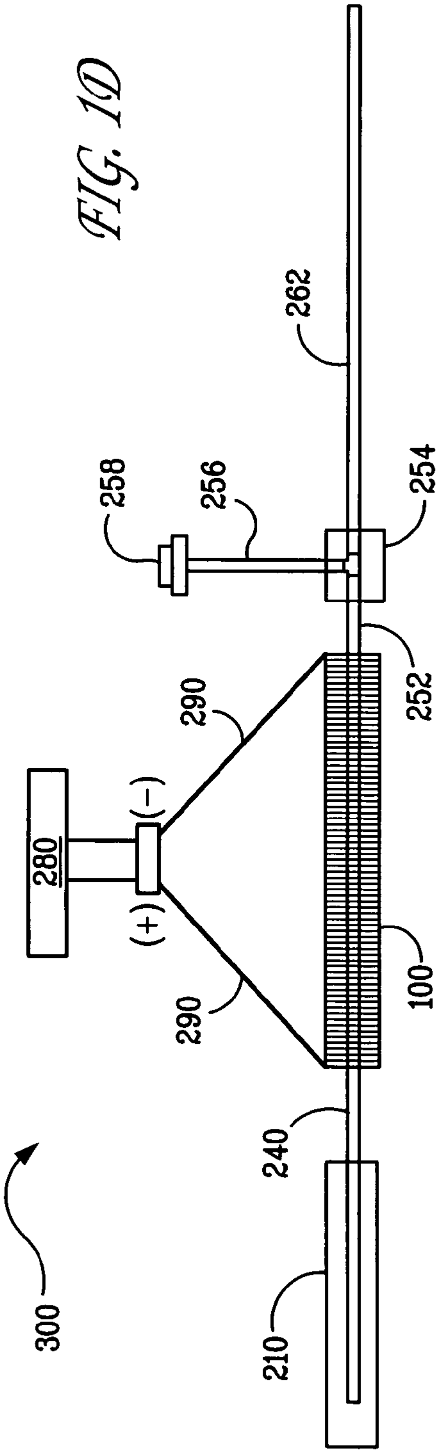
FIG. 1D is a schematic illustration of an embodiment of a sample preparation module of the present invention.
Figure 1E:
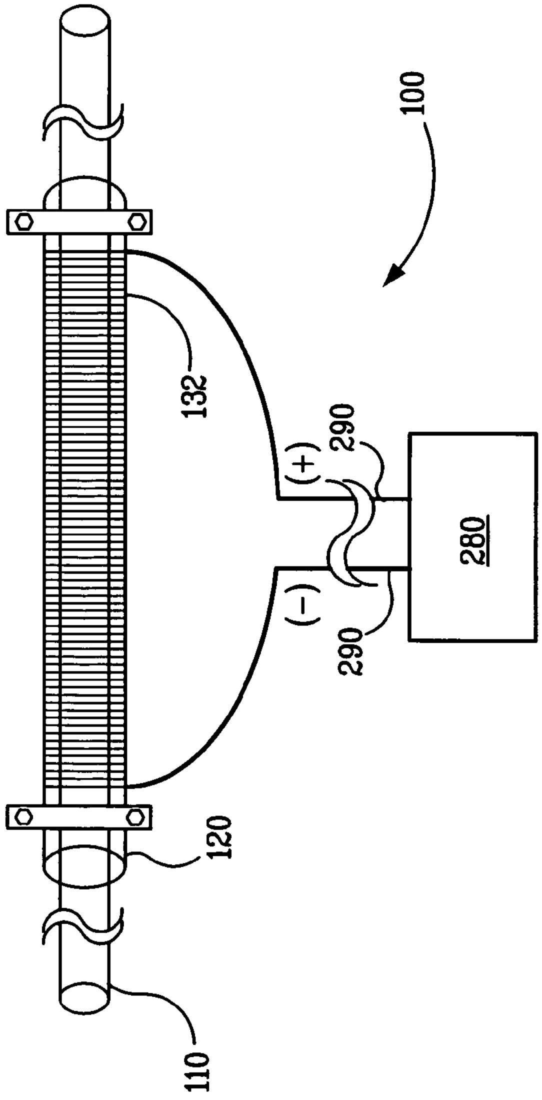
FIG. 1E is a schematic illustration of an embodiment of a lysing device of the present invention.

Another embodiment of the thermal lyser 100 is depicted in FIG. 1E. Here, inner conduit 110 is depicted interior to the lumen of outer conduit 120. Heating wire 132 is shown wrapped around the outer conduit and connected to power source 280 through electrical leads 290.

Another embodiment of the sample preparation module is depicted in FIG. 1D. Here, biological material source and pump 210 is fluidically connected through inlet conduit 240 to thermal lyser 100. A conduit 252 connects the exit of thermal lyser 100 to a fluidic connector 254, which is connected to a pressure transducer 258 through conduit 256. A flow restriction device 262 is connected to fluidic connector 254 for increasing the pressure within the thermal lyser. A suitable flow restriction device suitably includes a long, narrow capillary, for example, those having dimensions from about 5 to about 100 micron inner lumen diameter, and about 5 to 200 cm in length. In one embodiment, a flow restriction device comprising a capillary of a 27 micron inner diameter, 29 cm long provides a pressure of about 320 psi in the lyser for a flow rate of about 5 microliters per minute. For example, the boiling point of water is about 212° C. at 320 psi. The pressure typically increases proportionally with the flow rate and with the length of the flow restriction device (e.g., capillary).

Figure 4:
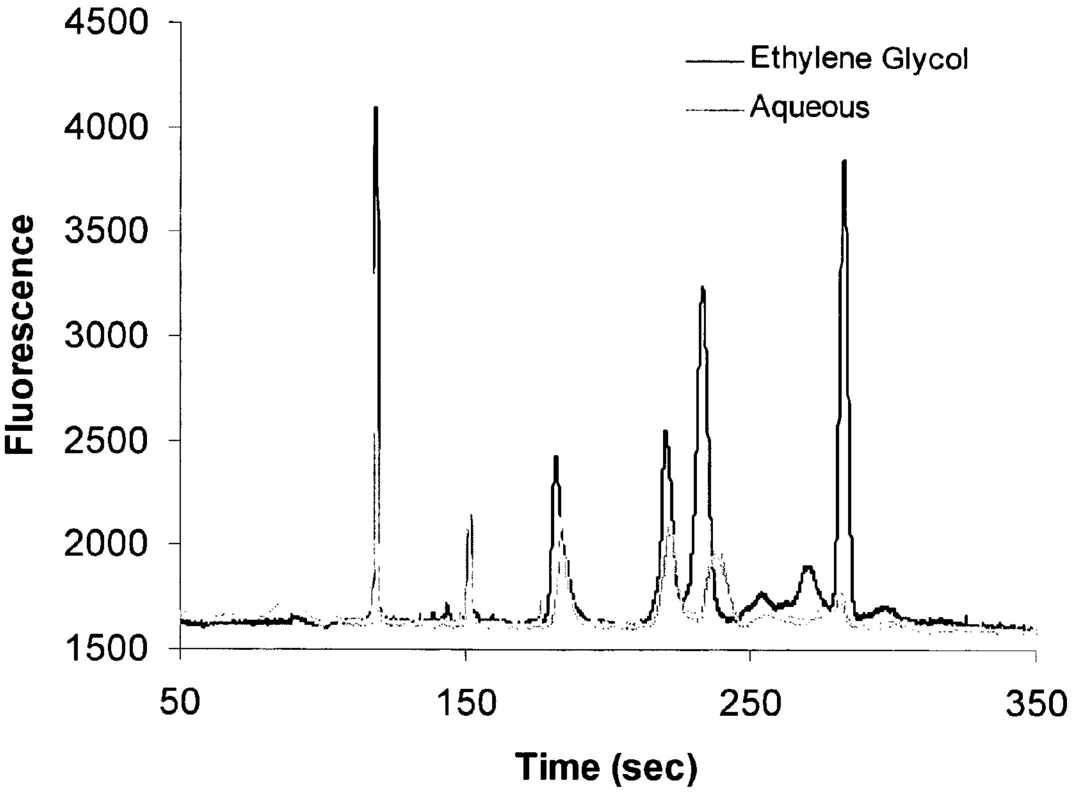
FIG. 4 compares fluorescence intensity versus time for a dye-labeled protein sample in aqueous and ethylene glycol solutions. A marked increase in peak area count protein samples suspended in ethylene glycol and mixed directly with the 10 mM fluorescein dye in dry acetonitrile, and then later diluted with the standard aqueous buffer.

The thermal lyser and the microanalytical device were integrated using a rapid reacting dye (fluorescent label, e.g., fluorescamine) in a solution that contained high concentrations of ethylene glycol. With regard to the thermal lyser, the concentration of fluorescamine dye was significantly higher in this configuration. When using the integrated system, the dye solution is added prior to the dilution of the sample with electrophoresis buffer. Without being bound by any particular theory of operation, it is believed that because the dye was added into a solution that was primarily ethylene glycol based, much higher concentration of dye could be used without the dye precipitating out of solution, as occurs when using the dye in an aqueous based buffer. In this arrangement, the lysed samples exiting the thermal lyser provided proteins, that were mixed directly with the 10 mM fluorescein dye in dry acetonitrile, and then later diluted with a standard aqueous buffer. A dramatic increase in the area counts of the detected peaks was observed using this protocol (FIG. 4). The mechanism behind this increase in signal to noise ratio of the detected peaks was investigated by evaluating the labeling efficiency of fluorescamine when using different buffers.

Figure 5:
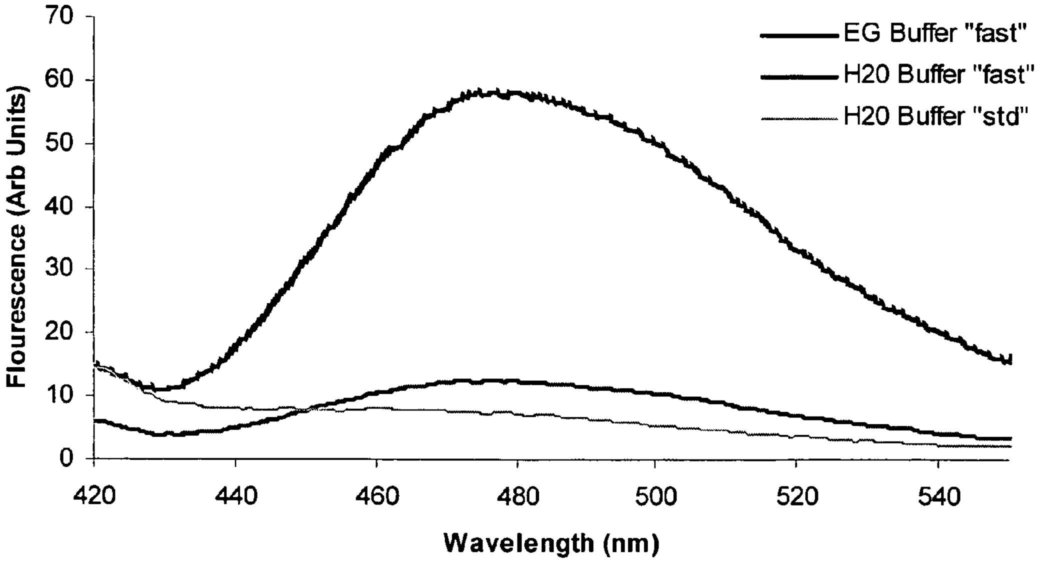
FIG. 5 illustrates a comparison of fluorescent light response of fluorescamine dye in different buffer solutions using an embodiment of the method of the present invention.

The use of fluorescamine to rapidly label protein as high as 10 μg in a 180 μL solution of 5 mM boric acid/5 mM SDS pH 8.5 buffer and later adding 20 μL 10 mM fluorescamine dye was reported by Renzi, R. F., et al., "Hand-portable analytical instrument for re-usable chip-based electrophoresis Part1: system design and integration", *Analytical Chemistry,* 2005; 77(2); 435-441. Using this protocol, a maximum fluorescent of 7.2 units was found at a peak wavelength of 475 nm, as seen as the EG Buffer "fast" line in FIG. 5. To determine the efficiency of the reaction in the ethylene glycol buffer, 20 μL of 10 mM fluorescamine in acetonitrile was added to 20 μL of ethylene glycol buffer containing 10 μg of bovine serum albumin (hereinafter "BSA") in 10 μL of water. Forty-five seconds after the addition of fluorescamine, standard aqueous buffer was added and the fluorescence spectrum was measured. These results are shown as the $H_2O$ Buffer "std" line in FIG. 5. A 45 second delay was used which is similar to the time used for mixing in the thermal lyser apparatus. Using this protocol an 8.0 fold increase (57.9 fluorescent units) in the production of fluorescence conjugates was observed over that of the standard aqueous buffer procedure ($H_2O$ Buffer "std" of FIG. 5). The same reaction was carried out using the 10 μg of BSA in a 20 μL solution of standard aqueous buffer as a one-to-one comparison. This reaction generated 12.4 fluorescent units of detectable products, and demonstrated a 4.7 fold increase in the conjugate labeling efficiency with the ethylene glycol buffer over that of the modified aqueous procedure ($H_2O$ Buffer "fast" of FIG. 5).

Figure 6A:
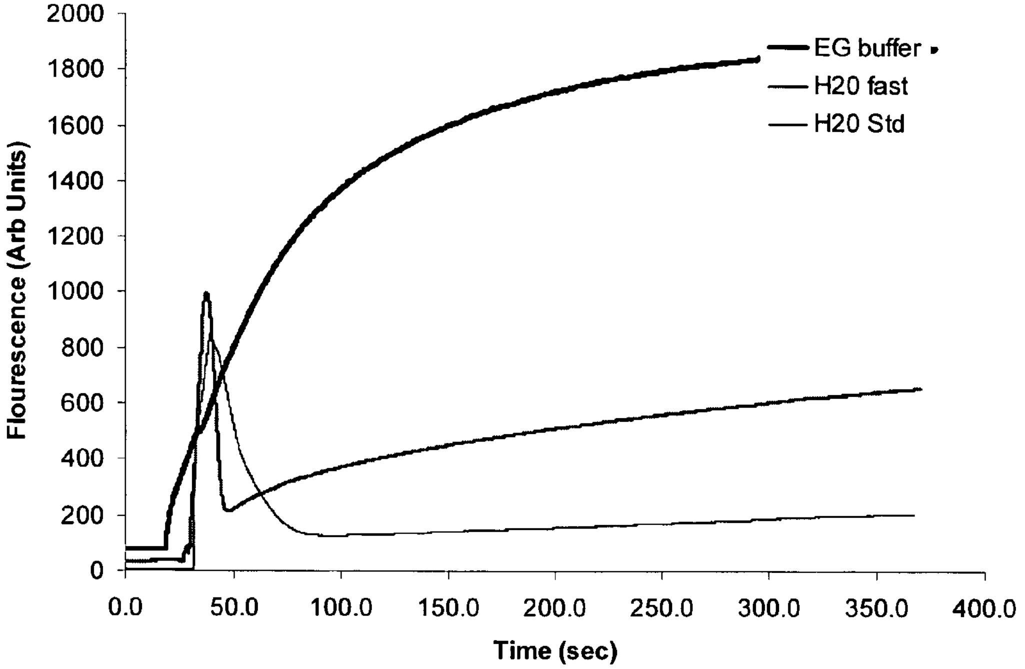
FIG. 6A shows the rate of fluorescent light increase with time for the different buffer solutions of FIG. 5.
Figure 6B:
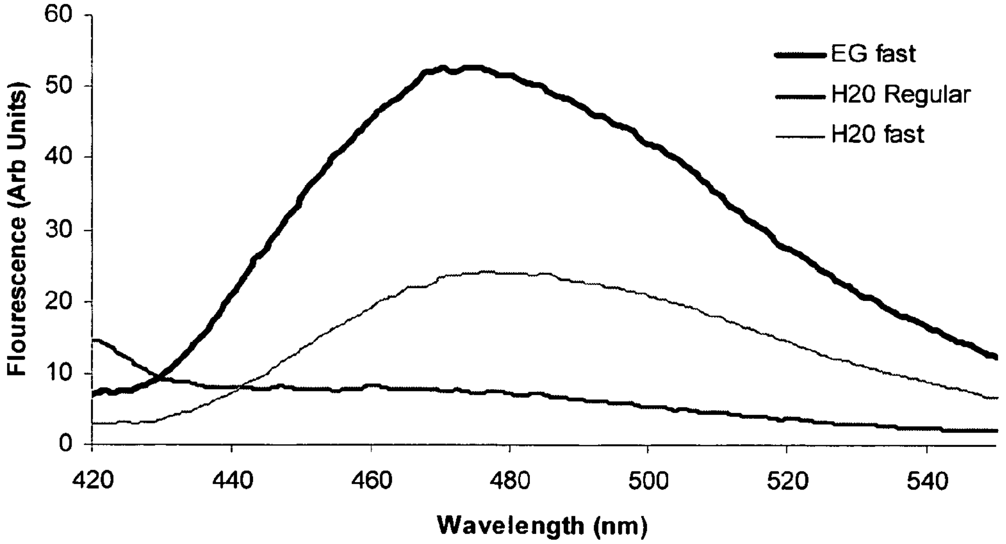
FIG. 6B illustrates a comparison of fluorescent light response of fluorescamine dye in different buffer solutions at a time later than 45 seconds showing the same relative behavior as the light response seen in FIG. 5.

The kinetics of fluorescent conjugate reaction were then determined by observing the fluorescent product generation as a function of time. Higher volumes of fluorescent product were generated for determining these kinetics. The first reaction was carried out in 280 μL of standard aqueous buffer with 10 μg of BSA in 10 μL of water, labeled with 20 μL of 10 mM fluorescamine in acetonitrile (FIG. 6A). An early dramatic increase of fluorescence attributed to dye precipitant was readily observed in the cuvette. The initial fluorescent signal decreased rapidly over 50 seconds to approximately 10 percent of its peak value. Without being bound to a particular theory of operation, this rapid decrease in signal was apparently attributed to the dye precipitant dissolving back into solution. A gradual increase in the fluorescent product formation over time was subsequently observed. The spectra of this reaction measured as a function of wavelength resulted in a peak fluorescence of 5 units at a wavelength of 475 nm (FIG. 6B).

The second reaction was an approximation of the low volume labeling done on the capillary apparatus, which is a 1:1 ratio of lysate to labeling dye. To compare labeling rates between a standard aqueous buffer and ethylene glycol buffer the reactions contained 150 μL of buffer mixed with 150 μL of 10 mM fluorescamine in acetonitrile, and 10 μg of BSA in 10 μL of DI water. These reaction conditions for the aqueous buffer (black line) revealed a similar pattern as compared to the first reaction carried out (light grey line). When dye was added a dramatic increase in fluorescence followed by a rapid decrease in fluorescence, which we also attribute to dye precipitation and re-solubilization. Similarly this was followed by a gradual increase in the fluorescent product formation over the time-course observed. This labeling strategy resulted in roughly three-fold increase in labeling efficiency as seen at the end of time-course (FIG. 6A) which was then confirmed by comparison of fluorescence spectra taken at completion of reaction (FIG. 6B). Without being bound by a particular theory of operation, the three fold increase in fluorescent product formation is apparently due to a three-fold increase in dye concentration in the second reaction.

The third reaction was carried out in the same manner as the second reaction, with 150 μL of ethylene glycol buffer, 150 μL of 10 mM fluorescamine in acetonitrile, and 10 μg of BSA in 10 ul of water. The largest difference to note is the lack of dye precipitation and a much faster increase in the fluorescent product formation, which appeared maximal at 300 seconds. The first two reactions did not reach maximal fluorescence until 600 seconds as measured in FIG. 6B. At the conclusion of the time-course we noted about a two-fold increase in fluorescent product formation at 475 nm between the ethylene glycol and water based buffers. Also it should be noted that the ethylene glycol buffer provided a seven-fold increase over the conventional labeling strategy.

The dye course, buffer source, and microanalytical device were integrated as a system with the thermal lyser of FIG. 1B. Protein signatures of a variety of agents could be rapidly generated using this system.

Figure 7A:
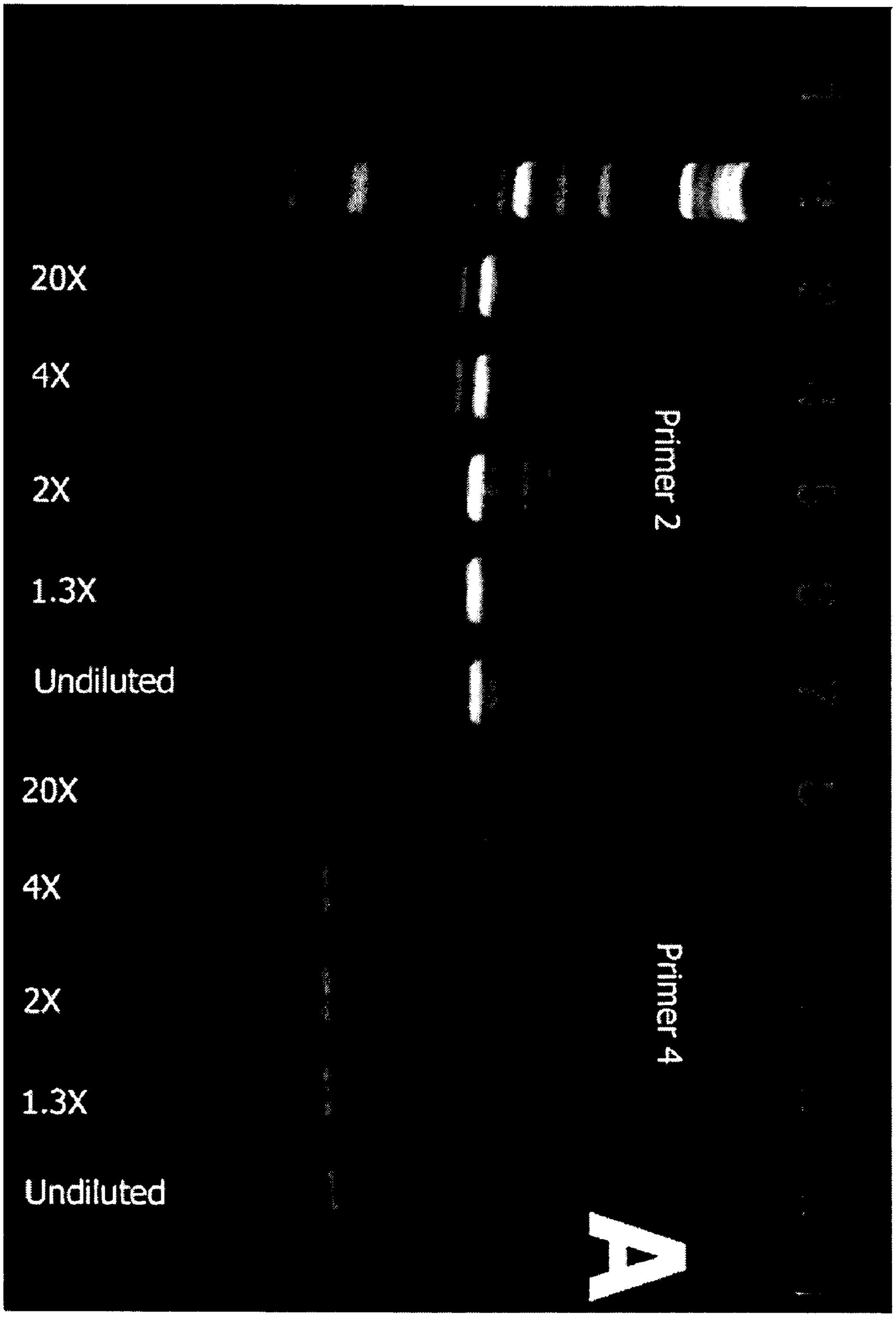
FIGS. 7A-7D shows various polymerase chain reaction experimental results of lysed and unlysed *Bacillus anthrasis* spores using various embodiments of the methods and devices of the present invention.

PCR reactions of *Bacillus anthrasis* lysate dilutions were performed to determine the amount of lysate needed to obtain products and also to visualize the banding pattern produced by each set of random primers. PCR analysis was performed using the Ready-To-Go™ RAPD analysis kit obtained from Amersham Biosciences (Piscataway, N.J.). A PCR reaction was carried out using a lysate that was initially diluted 1:16. PCR was performed with this sample along with a series of further dilutions (1:1.3, 1:2, 1:4, and 1:20). Two sets of PCR were carried out, one using primer 2 (herein 5'-d[GTTTCGCTCC]-3') (SEQ. ID. NO. 1) and the other using primer 4 (herein 5'-d[AAGAGCCCGT]-3') (SEQ. ID. NO. 2). Results are shown in FIG. 7A.

Figure 7B:
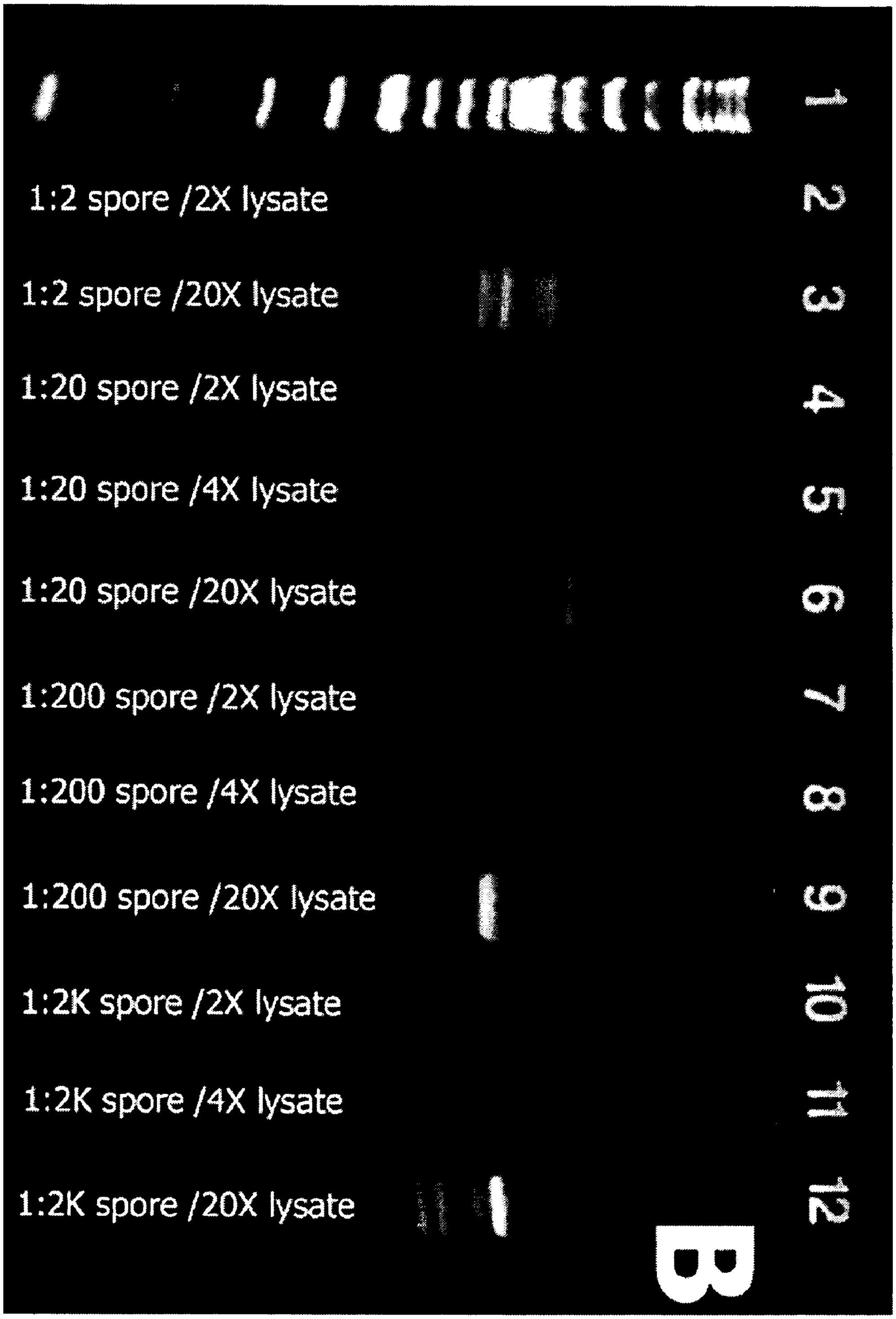

A second reaction set was carried out using dilutions of the spores that were used during lysis. Spore dilutions included 1:2, 1:20, 1:200, and 1:2000. Dilutions for each of the lysate included 1:1.3, 1:2, 1:4, and 1:20. Primer 2 was chosen for this analysis. Results are shown in FIG. 7B. A product from all dilutions (2-2000×) of the concentrated lysate could be obtained. Apparently, in this PCR experiment on the dilutions of spores, ethylene glycol inhibited the PCR reaction when present in high concentrations. The ethylene glycol concentrations present in the dilutions were 42% for the 1:1.3 dilution, 28% for the 1:2 dilution, 14% for the 1:4 dilution, and 2.8% for the 1:20 dilution. Not being bound by any theory of operation, PCR products were obtained from the 1:20 dilutions because the ethylene glycol concentration was too high in the other dilutions to allow for the PCR to take place. Therefore, 1:20 dilutions were used in the remaining experiments.

Figure 7C:
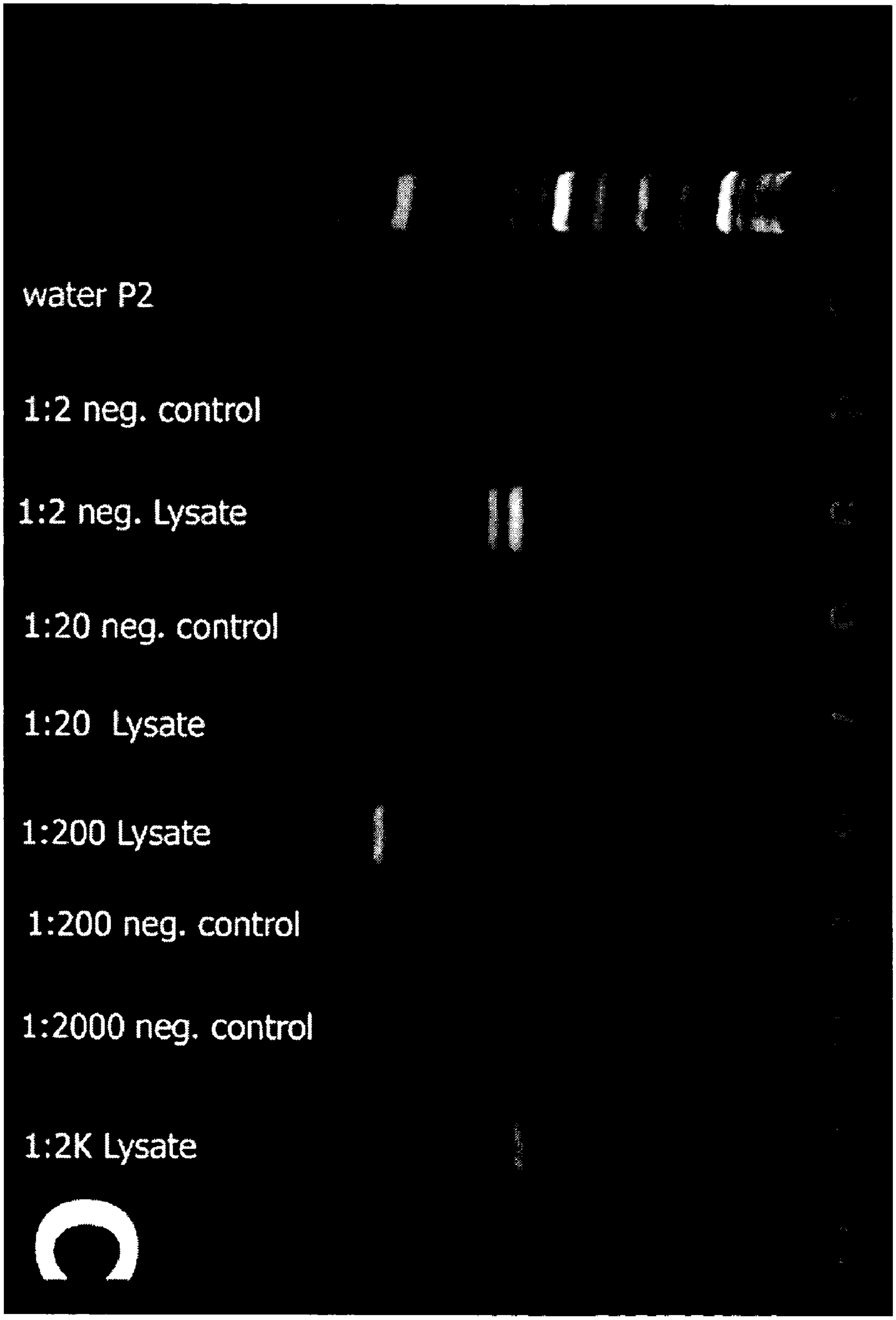

A third set of reactions were carried out using the same spore dilutions as used in reaction set two in order to be sure that the PCR products were obtained from DNA from lysed spores, reactions were run using unlysed spores as well as lysed spores. PCR was run on the lysate after a 1:20 dilution. Results provided in FIG. 7C show apparently no products formed from the solutions when unlysed spores (negative control) were used as a template at any of the dilution factors. These results show that the PCR products are indeed obtained from DNA of the lysed spores. The highest dilution (1:2000) contained template from as low as 295 spores.

Figure 7D:
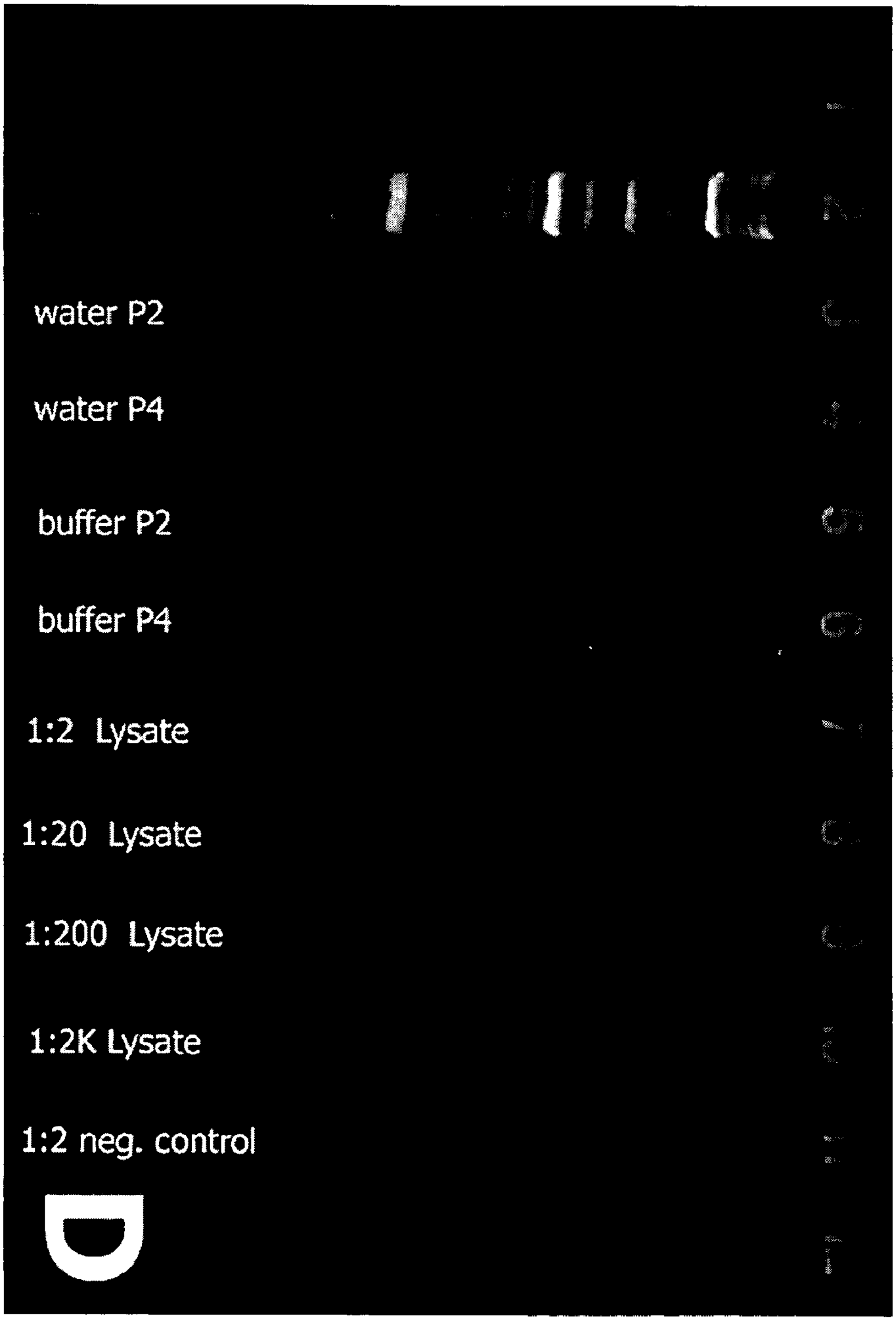

Separate solutions comprising pre-lysed spores, buffer at a 1:20 dilution, as well as water, were used as controls. These results are shown in FIG. 7D. Two sets of PCR were carried out, one using primer 2 and the other using primer 4. Without being bound by a particular theory of operation, the bands that are visible in the water control are most likely due to small amounts of DNA contamination in the polymerases. The presence of template DNA, however, out-competes this contamination and, as a result, these bands are not seen when the template is included. Without being bound by a particular theory of operation, the differences in banding patterns seen within the spore and lysate dilutions apparently arose from different primer:template ratios.

End products generated in each of the four reaction sets were visualized on a 2% agarose E-Gel obtained from Invitrogen Corporation (Carlsbad, Calif.).

Figure 8A:
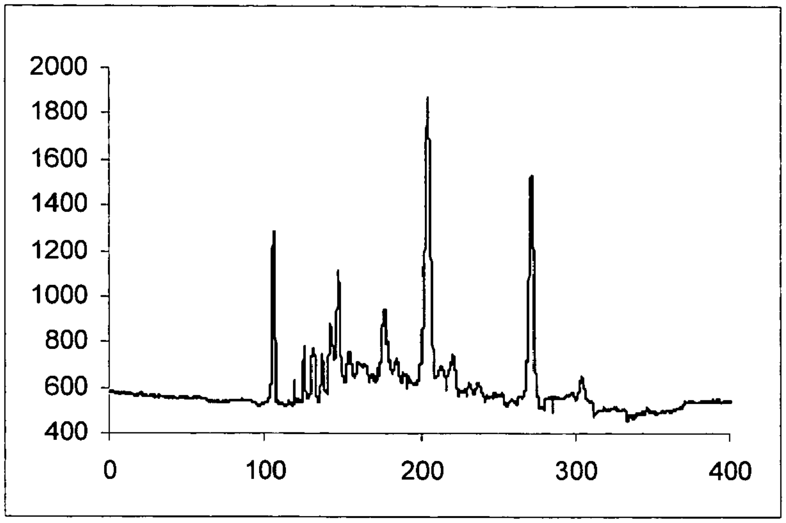
FIG. 8A shows the separation signature of T2 phage using various embodiments of the methods and devices of the present invention.
Figure 8B:
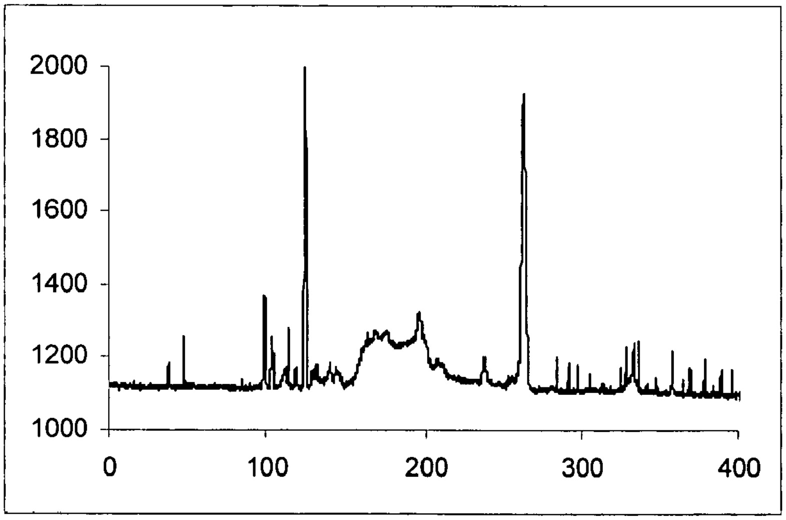
FIG. 8B shows the separation signature of *Bacillus subtilis* lysed at approximately 150° C. using various embodiments of the methods and devices of the present invention.
Figure 8C:
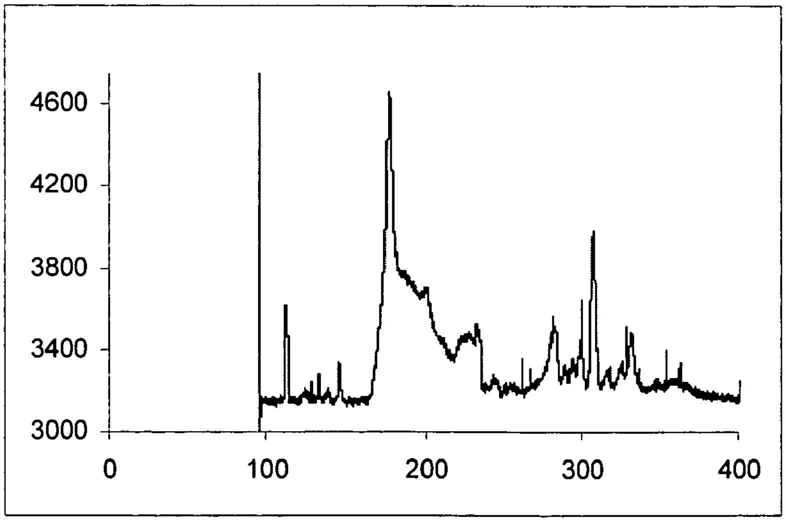
FIG. 8C shows the separation signature of *Bacillus subtilis* spores lysed at approximately 175° C. using various embodiments of the methods and devices of the present invention.

Using the thermal lyser apparatus and the in-line sample preparation set-up, protein signatures for viral agents, vegetative bacterial cells and bacterial spores were generated. First, T2 bacteriophage was processed through the device. After lysis (@100° C.), dye reaction and buffer dilution, the labeled lysate solution was applied directly to a μChemLab™ microanalytical system using a capillary connection. After sample loading, the sample was electrokinetically injected on to the separation column of the μChemLab™ chip. Further details of the design and operation of the μChemlab™ microanalytical system and chip are provided in U.S. Ser. No. 10/795,549, the entirety of which is incorporated by reference herein. The separation of the injected analytes revealed a signature of the T2 phage (FIG. 8A). This signature was in good agreement with previously conventionally processed samples. A similar lysis and sample preparation was conducted for vegetative bacteria and bacterial spores using elevated temperatures to perform lysis of these robust species. Vegetative *Bacillus subtilis* (FIG. 8B) was lysed at approximately 150° C. *Bacillus subtilis* spores (FIG. 8C) were lysed at approximately 175° C. Reproducible protein signatures of these agents were subsequently generated.

The foregoing experimental results indicate that rapid cell lysis and sample preparation can be performed using the methods and devices of the present invention, which are readily adapted for protein and DNA analysis in a portable system. Vegetative bacterial cells, bacterial spores as well as bacteriophage viruses could be robustly lysed and solubilized using the thermal lysers and methods described herein. Direct integrated protein fingerprinting analysis of these agents was possible by microcapillary gel electrophoresis ("mCGE"). Additionally, the detection of PCR products of the genomic material from the same samples was possible using random primer amplification.

Certain aspects of the present invention provide an integrated sample preparation module (FIG. 1A, 300) capable of complete solubilization of robust bacterial spores for protein fingerprinting using a microfluidic device. Several additional advantages have been identified using these various systems. One additional advantage is that this protocol, as seen in FIGS. 6A and 6B, could be used for a variety of agents, including vegetative bacteria and viral species. Processing these samples is readily achieved by adjusting the internal temperature of the inner conduit of the thermal lyser to achieve suitable solubilization conditions for an individual agent. Lower temperatures (about 95° C.) are typically used for lysing and solubilizing viruses. Slightly higher temperatures (about 125° C.), and the highest temperatures (about 175° C.) are typically used for spore lysis.

Several unexpected advantages of using a non-aqueous based buffer for sample processing were also observed. Although an initial concern was that the covalent labeling reaction kinetics could result in inefficient labeling of the proteins due to dye precipitation in the spore and virus lysates, it was surprisingly found that the devices and methods of the present invention could perform the dye labeling reaction in a ten-fold less volume that that of the protocol of Renzi, R. F., et al., "Hand-portable analytical instrument for re-usable chip-based electrophoresis Part1: system design and integration", *Analytical Chemistry,* 2005; 77(2), pp. 435-441. Without being bound by any particular theory of operation, this low volume sequential labeling step was superior when labeling in either standard aqueous buffer or in the ethylene glycol based buffer, as it appeared that the increased protein concentration of the sample outweighed the problem of dye precipitation in the reaction. Additionally, the fluorescamine labeling of protein in ethylene glycol was superior, in terms of kinetics and overall labeling efficiency to the labeling process performed in water based buffers. This improvement in the labeling efficiency apparently results from the absence of competing hydrolysis reactions and dye precipitation in the standard aqueous based buffers. This was surprising given the considerably higher viscosity of the ethylene glycol buffer. This demonstrates that the reaction carried out in ethylene glycol was not detrimental to covalent fluorescamine labeling. The intensity of the fluorescent product generated in ethylene glycol based buffer was statistically higher compared to the water based buffer.

The results also demonstrate that higher molecular weight proteins appear to be more extensively labeled using the ethylene glycol-based buffer. Without being bound by any particular theory of operation, this may also result from the decrease or absence of competing hydrolysis reactions which allow for the larger sized proteins to be more efficiently labeled in the ethylene glycol buffer.

Many detection platforms for identifying biological agents are based on DNA analysis. The thermal lysers, systems and methods of the present invention have the capability to prepare samples not only for protein fingerprinting but also for the direct amplification of DNA from the elutants of lysed agents. As seen in FIGS. 7A-D, the lysed samples were subsequently analyzed for genomic containing material. Using a random primer with the disclosed methods, one is able to specifically amplify DNA from lysed *Bacillus anthrasis*. Initial attempts to purify DNA from these samples resulted in a relatively low efficiency of extraction. In an effort to perform the amplification, determining whether the elutant could be used directly in a PCR reaction was tested. It was found that while ethylene glycol inhibited the reaction at high concentration (greater that 4%), this inhibition could be overcome by diluting the spore lysate in PCR buffer. To determine the limit of detection, both dilutions of high concentration spore lysates and dilutions of spores that were lysed in low concentration were performed. A calculated limit of detection using the random primer PCR was about 300 spores.

One of the many goals of the present invention was to develop methods that lyse, solubilize and label robust spores for protein analysis. Not only are such methods provided herein, but also these methods can be extended to other vegetative bacterial cells and viruses. Additionally, using the methods, systems and devices of the present invention, one can perform PCR amplification of DNA from the same samples. Without being bound by a particular theory of operation, ethylene glycol appears to interfere with the purification and subsequent analysis of both proteins and DNA in these samples using conventional techniques. The mechanism of this interference is not certain, but it may result from the absence of charged species in the lysing solution. While the increased boiling temperature of ethylene glycol over that of water affords the ability to superheat these solutions and subsequently lyse robust spores, it appears that the present methods can be extended further. Such extensions can include using other high boiling point solvents that may have less interaction or interference with the analytes of interest. The current system can also be readily optimized by one of skill in the art with real-time PCR assays, and immunological reagent based detection assays.

The examples provided herein have demonstrated that efficient lysing and complete solubilization of viruses, vegetative bacteria and bacterial spores is possible using the methods, devices, and systems of the present invention, including direct integration with microfluidic devices. The methods of the present invention allow for rapid analysis, for example about ninety seconds for spore lysis, fluorescamine labeling and buffer dilution, and less than about six minutes for analysis. The methods, thermal lysers and systems of the present invention enable the universal preparation of biological organisms, labile or robust, for subsequent analysis by either protein or DNA analysis.

Without being bound to a particular theory of operation, several factors that may increase the labeling efficiency include, for example, 1) mixing steps and 2) the use of a non-aqueous based buffer. The labeling reaction can be optimized through the use of low volume high concentration dye solutions. In performing such reactions, the solution used for the labeling reaction allows the dye to remain dissolved in the solution (i.e., not precipitated) to be available to react with the protein or DNA analytes. Ethylene glycol based buffer was found to be a suitable solvent that enabled the performance of the reactions with high dye concentrations, which resulted in improved labeling kinetics and fluorescent product generation.

In another embodiment there is provided a thermal lyser formed using layers of material that contain one or more inner conduits and heaters that are laminated together. Referring to FIG. 9A, there is provided a thermal lyser composed of a bottom layer 400, a lower intermediate layer 402, a middle layer 403, an upper intermediate layer 404, and a top layer 405. The middle layer 403 has one or more fluidic microchannels 412 formed therein which have a microchannel sealing wall formed by adjacently sealing the lower and upper intermediate films 402 and 404, respectively. Suitable materials for the layers include glass, plastic, silicon, ceramic, composites thereof, and preferably glass-ceramic composite materials, for example a combination of ceramic and crystallizing glasses, for high temperature lysing of biological agents like cells, viruses, and spores. This embodiment has an integrated resistive heater, for raising the temperature in the fluidic microchannel from room temperature to above 100° C., and preferably above 200° C. The pressure in this device can also be elevated to increase the boiling point of the carrier fluid. For example, conditions of 185° C. at 160 psi in the ceramic lyser are typically sufficient to lyse robust agents (i.e., bacterial spores) with minimal damage or degradation to internal proteins and DNA for further analysis. Although this embodiment uses five layers, fewer or more layers are envisioned, for example, the fewer layers are envisioned when the two or more layers are integrated.

In another embodiment, fluidic microchannels can be fabricated in substrates using a sacrificial volume material ("SVM"). Suitable sacrificial materials can be used as a place-holder during lamination that burns away cleanly in the firing sequence, leaving a void that provides a microchannel. For example, referring to FIG. 9A, stripes of SVM can be applied to middle layer 403 to form microchannels 412.

Figure 9B:
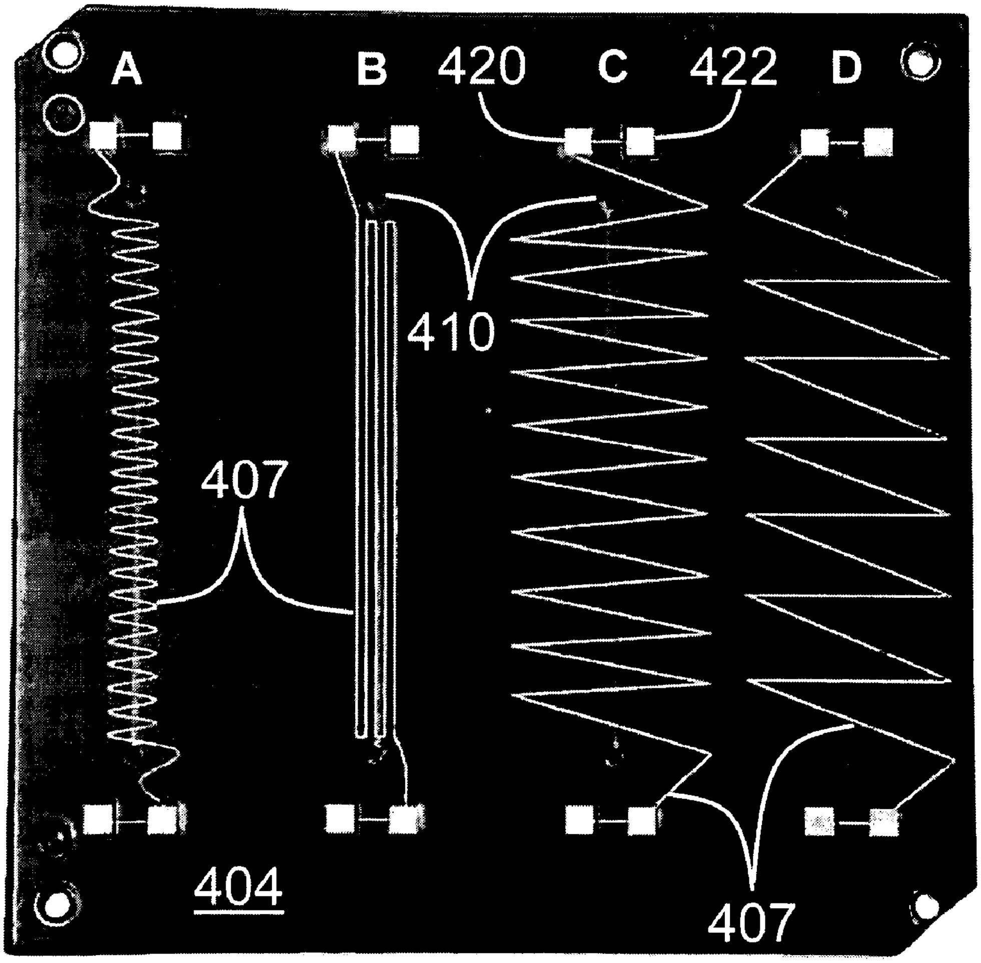
FIG. 9B shows four various types of heater trace patterns, A (sinusoidal), B (serpentine), C (regular sawtooth) and D (irregular sawtooth) used in several embodiments of the invention.

Fabrication of a ceramic-based layered microfluidic thermal lyser. A ceramic lyser was fabricated using a low-temperature cofired ceramic material ("LTCC") or a high-temperature cofired ceramic material ("HTCC"). HTCC is commercially available from ESL Electro-Science, King of Prussia, Pennsylvania. LTCC is commercial available from Dupont® Corporation and sold under the tradename of Green Tape™. Green Tape™ material system is a co-fired glass/ceramic dielectric substrate combined with an organic binder. LTCC material is particularly useful in microfluidic applications because of its physical properties of high strength, inertness, low coefficient of thermal expansion, refired stability, and environmentally-safe binders and solvent system. LTCC substrates were made from discrete laminated sheets (400, 402, 403, 404, and 405) of Green Tape™. Referring to FIG. 9A, microchannels 412 were cut into substrate 403 and stacked between substrates 402 and 404 to form a three-dimensional cavity. This was held between upper substrate 405 and lower substrate 400. Additional features such as via holes 410, metal traces for heating film 406, 407, and electrical pass-thrus (FIG. 9B, 422) were incorporated at the time of lamination. Stacked layers were compressed with an isostatic hydraulic press and then placed in a high-temperature oven for sintering at 850° C. into a single monolith substrate. FIG. 9A shows how five layers of LTCC were used to fabricate a ceramic lyser.

FIG. 9A shows four individual lysers with four different heater configurations on LTCC substrate (also see FIG. 9B for heater configurations A-D). Substrate dimensions are approximately three inches by three inches square. In this example, each layer is 10 mils (0.010 inches, 250 microns) thick. The bottom layer 400 and the top layer 405 are external surfaces of the device. These layers help protect and insulate gold thick-film metalized traces (heating film) on the intermediate layers 402 and 404. Suitable materials for the heating film include metals such as gold, platinum, palladium, silver, and any combination thereof such as alloys, as well as resistor materials having low sheet resistance. Gold-based compositions are typically preferred. The middle is layer 403 with 0.010 inches wide punched microchannel. The two heater traces (406 and 407), above and below the microchannel, provide sufficient resistive heating into the microchannel. FIG. 9B shows four various types of heater trace configurations, A (sinusoidal), B (serpentine), C (regular sawtooth) and D (irregular sawtooth), each having metal heating traces 407, via holes 410, electrical contacts 420, and optional electrical pass-thrus 422. The down-facing thick film traces on the underside of substrate 402 and the up-facing metal traces on 404 typically have optional electrical pass-thrus 422 or another interconnect to make them the electrical traces electrically accessible through the adjoining substrates. In certain embodiments, electrical pass-thrus are not required as the electrical connections for the heater could be brought out to the edge of the substrate. In certain embodiments, two or more layers may communicate through contact or via holes filled with the heater material. Microchannel dimensions are nominally 0.010 inches by 0.010 inches after the substrate is fired. As used herein, the word "nominally" refers to the about 12% shrinkage in-plane and about 15% shrinkage out of plane upon firing of the substrate. FIG. 10 shows the temperature response curve with respect to applied voltage and current to an internal resistive heater. The top and bottom heater trace measure 80-90 ohms of resistance.

Use of ceramic microfluidic lyser. FIGS. 11(A-D) shows various views of two embodiments of a ceramic lyser: one with clamp-down o-ring sealed fittings (A and B), and one with epoxy-bonded fittings (C and D). At room temperature both are capable of withstanding pressures above about 1,000 psi internally. Another device made substantially the same as that shown in FIGS. 11A-D was capable of withstanding pressures of even about 5,000 psi. The epoxy-bonded fittings are capable of withstanding about 500 psi pressure when heated to about 150° C. Higher operating temperatures are possible at lower operating pressures. The clamp-down o-ring seal (see close-up in FIG. 11B) fitting has been pressure tested up to 800 psi at 220° C. with no failure. In certain preferred embodiments, the biological materials are lysed at pressures below 500 psi.

FIG. 12 shows a sample preparation system for lysing spores (*Bacillus subtilis*) at elevated pressure and temperature. A standard syringe pump and 250 uL syringe (not shown) delivers flow at 2-6 μL/min to the ceramic lyser 100 through conduit 240. Spores from a stock concentration of $10^8$/mL were diluted to a working concentration of $10^5$/mL for use with the ceramic lyser. An aqueous carrier fluid, for example water, can be used. For this example, borate buffer with 5 mM SDS at pH 8.8 was used. The suspension of spores entered the lyser 100 and traveled along a 1.5 inches long microchannel within the middle layer (not shown) that was heated to 185° C. The lysate exited through a capillary 252 to a tee union 254 where a pressure sensor 258 and capillary flow restrictor (27 μm~29 cm, not shown) are connected. Back pressure generated due to the flow restriction was approximately 160 psi at a flow rate of about 2.5 uL/min. At 160 psi the boiling point of water was raised to 180° C. The processed sample fluid exiting the lyser was not turbid, compared to the sample fluid entering the lyser. This lack of, or reduction in, turbidity evidences that the spores were lysed (see FIG. 13, photo). Subsequent centrifugation also resulted in no visible pellet formation, which indicates that the spores were lysed. The lysate was analyzed with capillary gel electophoresis for solubilized proteins to confirm the spores were lysed. FIG. 13, chart, also shows an electropherogram of spores lysed at 185° C. and 160 psi. The results show a good separation of proteins ranging in low to high molecular weight. Initial DNA spectrophotometric analysis also demonstrated that large quantities of solubilized DNA were also present.

In certain embodiments, the method of lysing uses substantially only heat for lysing cells. Particular advantages are apparent in view of the fact that chemical reagents are not needed in this embodiment. Without being bound to a particular theory of operation, high thermal energy apparently dissolves and break-apart the spore coat to release the spore contents. Various embodiments of the present invention establishes the use of elevated temperatures to demonstrate spore lysing using high thermal energy. Various embodiments use a capillary format and a coiled-wire heater wrapped exterior to an inner capillary through which the biological material flows and lyses. Certain of these embodiments use and organic solvent, such as ethylene glycol, as the carrier fluid to achieve temperature up to 190° C. to avoid boiling of the carrier fluid at ambient or slightly elevated pressures.

In certain embodiments, high temperatures without boiling can be achieved using a combination of high pressures and high temperatures. Temperatures above 100° C. and pressures above 1 atm (14.7 psi) can be easily achieved using layered constructs containing microchannels, especially using ceramic layers. Increasing the internal pressure in the microchannel increases the boiling point of water allowing high temperatures to be reached, eliminating the need for ethylene glycol carrier. Standard buffers can be used to have minimal interference with analysis techniques (i.e., PCR of DNA). The ceramic microfluidic device also provides a convenient integrated package with imbedded heaters. Simple current or voltage control can regulate the temperature inside the microchannel. As a modular component the ceramic device can be used as an in-line component of a flow-through system or used in a batch-process mode. The inexpensive, and easy fabrication of LTCC microfluidic substrates makes such devices suitable for disposable, single-use, applications. In additional embodiments, the thermal lyser devices can also include suitable electrical contact pads, plug-in electrical leads, electrical circuitry, electronic components, optoelectronic components, optical components, fluidic components, or any combination thereof.

What is claimed:

1. A device for lysing biological material, comprising:

an inner conduit for transporting the biological material, the inner conduit having an entrance and an exit, the inner conduit being characterized as a capillary tube or a microchannel; and a heater situated exterior to the inner conduit capable of heating the biological material to at least about 125° C. while the biological material is transported within said inner conduit.

2. The device of claim 1, further comprising an outer conduit surrounding the inner conduit.

3. The device of claim 2, wherein said heater comprises a heating coil wrapped around the outer conduit.

4. The device of claim 1, wherein the microchannel resides in a first substrate layer and the heater comprises a metal trace formed on a second substrate layer, both the first and second substrate layers being bonded together.

5. The device of claim 1, wherein the heater is capable of heating the biological material to a temperature of at least about 200° C.

6. A micro-total analysis system, comprising:

an analytical device, and a system for delivering biological material to the analytical device, comprising:

a biological material source;

a thermal lyser comprising an entrance and an exit, the entrance being in fluid communication with the biological material source, the thermal lyser capable of heating the biological material to at least about 100° C. while the biological material is transported within the thermal lyser;

a dye source in fluid communication with the exit of the thermal lyser;

a buffer source in fluid communication with the exit of the thermal lyser; and an exit capable of being in fluid communication with the analytical device.

7. The micro-total analysis system of claim 6, wherein the analytical device is capable of analyzing biological material using electrophoresis.

8. A method of preparing a biological sample for analysis, comprising:

flowing a biological sample fluid comprising biological material and a solvent through a conduit;

heating the biological sample fluid as it flows through said conduit to greater than 100° C. at a pressure greater than 1 atmosphere;

lysing at least a portion of the biological material; and labeling at least a portion of the lysed biological material with a dye.

9. The method of claim 8, wherein the biological material includes bacterial cells, bacterial spores, viruses, animal cells, plant cells, or any combination thereof.

10. The method of claim 8, wherein the solvent comprises water, an organic solvent, or any combination thereof.

11. The method of claim 8, wherein the solvent consists essentially of water, ethylene glycol, or any combination thereof.

12. The method of claim 8, wherein the biological sample is heated to at least about 125° C.

13. The method of claim 8, wherein the residence time of the biological material as it is heated is up to about 300 seconds.

14. The method of claim 8, further comprising at least one PCR step.

15. The method of claim 14, wherein the concentration of organic solvent present during the PCR step is less than at out 3%.

16. A method of analyzing a biological sample, comprising:

flowing a biological sample fluid comprising a biological material and a solvent at a pressure greater than 1 atmosphere;

heating the biological sample fluid to greater than 100° C. as it flows;

lysing at least a portion of the biological material to release biomolecules;

labeling at least a portion of the biomolecules with a dye; and measuring the molecular distribution of the labeled biomolecules.

17. The method of claim 16, wherein the solvent comprises water, an organic solvent, or any combination thereof.

18. The method of claim 17, wherein the solvent consists essentially of water, ethylene glycol, or any combination thereof.

19. The method of claim 17, wherein the molecular distribution is measured using capillary electrophoresis.

20. The method of claim 16, wherein the dye is a rapid reacting dye.

* * * * *